US011982675B2

(12) United States Patent
Szabó et al.

(10) Patent No.: US 11,982,675 B2
(45) Date of Patent: May 14, 2024

(54) METHOD OF ASSESSING ABC TRANSPORTER ACTIVITY USING FLUORESCENT DYE ACCUMULATION ASSAY

(71) Applicants: CELLPHARMA KFT., Budapest (HU); TERMÉSZETTUDOMÁNYI KUTATÓKÖZPONT, Budapest (HU)

(72) Inventors: Edit Szabó, Budapest (HU); Dóra Kovács-Türk, Budapest (HU); Ágnes Telbisz, Budapest (HU); Nóra Kucsma, Budapest (HU); Tamás Horváth, Budapest (HU); Gergely Szakács, Budapest (HU); László Homolya, Telki (HU); Balázs Sarkadi, Budapest (HU); Várady György, Budapest (HU)

(73) Assignees: CELLPHARMA KFT., Budapest (HU); TERMÉSZETTUDOMÁNYI KUTATÓKÖZPONT, Budapest (HU)

(*) Notice: Subject to any disclaimer, the term of this patent is extended or adjusted under 35 U.S.C. 154(b) by 354 days.

(21) Appl. No.: 16/759,422

(22) PCT Filed: Oct. 25, 2018

(86) PCT No.: PCT/HU2018/050046
§ 371 (c)(1),
(2) Date: Apr. 27, 2020

(87) PCT Pub. No.: WO2019/081957
PCT Pub. Date: May 2, 2019

(65) Prior Publication Data
US 2020/0284797 A1 Sep. 10, 2020

(30) Foreign Application Priority Data
Oct. 25, 2017 (HU) .................................. P1700432

(51) Int. Cl.
*C07K 14/705* (2006.01)
*C12P 17/06* (2006.01)
*G01N 21/64* (2006.01)
*G01N 33/50* (2006.01)
*G01N 33/58* (2006.01)
*G01N 33/60* (2006.01)

(52) U.S. Cl.
CPC ......... *G01N 33/582* (2013.01); *C07K 14/705* (2013.01); *C12P 17/06* (2013.01); *G01N 21/64* (2013.01); *G01N 33/5035* (2013.01); *G01N 33/60* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

| 5,872,014 A | 2/1999 | Sarkadi et al. |
| 7,122,329 B2 | 10/2006 | Homolya et al. |
| 2020/0284797 A1* | 9/2020 | Szabó .................. G01N 33/582 |

FOREIGN PATENT DOCUMENTS

WO 2009/052183 A1 4/2009

OTHER PUBLICATIONS

Hegedüs et al.: "Ins and outs of the ABCG2 multidrug transporter: An update on in vitro functional assays", Advanced Drug Delivery Reviews, 2009, vol. 61, pp. 47-56.
Homolya et al.: "Fluorescent Cellular Indicators are Extruded by the Multidrug Resistance Protein", J Biol Chem, 1993, vol. 268 (29), pp. 21493-21496.
Delmar et al.: "Bacterial multi-drug efflux transporters", Annual Review of Biophysics, 2014, 43:93-117.
Lebedeva et al.: "Sensitive and Specific Fluorescent Probes for Functional Analysis of the Three Major Types of Mammalian ABC Transporters", PLoS ONE, 2011, vol. 6, doi:10.1371/journal.pone. 0022429.
Molecular Probes Handbook—11th Edition (2010) Chapter 19 "19.7 Indicators for Copper—Phen Green indicators", pp. 844 and 880.
Nerada et al.: "Application of Fluorescent Dye Substrates for Functional Characterization of ABC Multidrug Transporters at a Single Cell Level", Cytometry Part A, 2016, vol. 89(9), pp. 826-834.
Petrat et al.: "Determination of the Chelatable Iron Pool of Isolated Rat Hepatocytes by Digital Fluorescence Microscopy Using the Fluorescent Probe, Phen Green SK", Hepatology, 1999, vol. 29, No. 4, pp. 1171-1179.
Strouse et al.: "Fluorescent substrates for flow cytometric evaluation of efflux inhibition in ABCB1, ABCC1, and ABCG2 transporters", Anal Biochem., 2013, vol. 437, pp. 77-87.
Türk: "Identification and in vitro investigation of compounds that selectively kill multidrug resistant cancer cells", Ph.D. Thesis; Eötvös Loránd University, Faculty of Science, Doctoral School in Biology, 2014, pp. 1-5.

* cited by examiner

*Primary Examiner* — Hope A Robinson
(74) *Attorney, Agent, or Firm* — Jason D. Voight

(57) ABSTRACT

ABC multidrug transporters are key players in cancer multidrug resistance and in general xenobiotic elimination, thus their functional assays provide important tools for research and diagnostic applications. It has been found that in cells expressing functional ABCG2, ABCB1, or ABCC1 transporters, cellular PG fluorescence is strongly reduced. The invention relates to methods and uses of fluorescein derivative ester compounds of formula Ia which are analogs of PG for assessing ABC transporter activity of ABC multidrug transporters. The present accumulation assay is a novel tool for the parallel determination of the function of the multidrug transporters, in particular ABCG2, ABCB1, and ABCC1. The assay is applicable for diagnostic purposes and also allows the selection, separation and culturing of selected cell populations expressing such transporters.

23 Claims, 21 Drawing Sheets

A. ABCB1 expressing PLB cells

B. ABCC1 expressing HL-60 cells

METHOD OF ASSESSING ABC TRANSPORTER ACTIVITY USING FLUORESCENT DYE ACCUMULATION ASSAY

TECHNICAL FIELD

The present invention relates to a fluorescent dye accumulation assay for parallel measurements of multiple ABC multidrug transporters, as efflux pumps, capable of extruding PhenGreen dyes. In particular, the invention relates to measurements of the ABCG2, ABCB1 and ABCC1 multidrug transporter functions via detecting accumulation of the fluorescent dye in a cell. The invention also includes a diagnostic application of the functional assays in normal and malignant human (blood) cells.

BACKGROUND ART

ABC multidrug transporters are key players in cancer multidrug resistance and in general xenobiotic elimination, thus their functional assays provide important tools for research and diagnostic applications. Several members of the ATP-binding cassette (ABC) superfamily of membrane transporters are working as efflux pumps for a large variety of xenobiotics and drugs. Therefore, these transporters are important players in multidrug resistance against anti-cancer therapeutic compounds, and also significantly modify the absorption, distribution, metabolism, excretion and toxicity (ADME-Tox) parameters for numerous therapeutic agents. The three key ABC efflux transporters involved in human cancer drug resistance and drug metabolism are the ABCB1 (P-glycoprotein, Pgp), the ABCC1 (multidrug resistance protein 1, MRP1) and the ABCG2 (breast cancer resistance protein, BCRP) proteins, thus their evaluation has a major importance in drug development and clinical diagnostics [Doyle L A et al. Oncogene. 2003; Sarkadi B et al. Physiol Rev. 2006; Dean M et al. Nat Rev. 2005; Szakács G et al. Drug Discov Today. 2008; Robey R W et al. Curr Pharm Biotechnol. 2012; Horsey A J et al. Biochem Soc Trans. 2016]. Due to the promiscuity of these proteins in drug binding and transport, the molecular mechanisms of drug interactions and the potential drug-drug interactions caused by the expression and function of these transporters are largely unexplored. Recent structural and modeling data for these ABC transporters [Taylor N M I et al. Nature. 2017; László L et al. PLoS One. 2016] are still insufficient to predict substrate interactions at a molecular level, thus experimental techniques to assess these interactions are of utmost importance.

Data on ABC multidrug transporter protein expression and localization have to be complemented with efficient functional assays in order to evaluate the potential effects of transporters on drug interactions. There are various assays assessing the function of these ABC transporters, including drug-stimulated ATPase activity, direct drug transport measurements in whole cells or in inverted membrane vesicles, and a widely applied assay system is to follow the extrusion of fluorescent transporter substrates from living cells [Hegedűs C, et al. Adv Drug Deliv Rev. 2009; Strouse J J et al. Anal Biochem. 2013]. Transporter substrate dyes, becoming fluorescent when interacting with cellular DNA (e.g. Hoechst 33342 or DCV), have been efficiently used to study the cellular function of these transporters [Strouse J J, see above, Telford W G et al. Stem Cells. 2007; Boesch M et al. Cytom Part 2012; Boesch M et al. Stem Cells Int. 2016 Nerada Z et al. Cytom Part A. 2016], but these compounds have long-term toxic effects and no such dye has been found as a common substrate for all the three major ABC drug transporters. A transporter assay was reported with unpublished structures of the dyes, eFluxx-IDH Green and Gold, suggesting a parallel examination of the three multidrug transporters, although this dye has relatively high toxicity [Lebedeva I V et al. PLoS One. 2011].

A significant amplification of the sensitivity of the cellular transporter assays is achieved when the substrate extruded by the ABC transporter is non-fluorescent, and the cellular metabolism-dependent accumulation of a highly fluorescent derivative is strongly reduced by the action of the transporter. Such an assay for ABCB1 and ABCC1, by using e.g. the non-toxic cell viability dye Calcein-AM, is already available [Homolya L. et al., 1993; Homolya L. et al. Br J Cancer. 1996; Karászi É et al. Br J Haematol. 2001; 112: 308-314. Sarkadi et al., EP0784699B1 Published in 1996; Sarkadi et al. U.S. Pat. No. 5,872,014 granted on Feb. 19, 1999]. This method is now widely used also for diagnostic applications in human blood cells and other tissue cells, including cancer cells.

In a study we have unexpectedly found that transport function of key human ABC multidrug transporters can be assessed with a cell permeable fluorescent metal ion indicator comprising a phenantroline moiety or an analog thereof linked to a 3',6' dihydroxi fluorescein fluorophore via carbon 5 or 6 of phenantrolin (or a carbon corresponding to 9 to 10 of the corresponding phenantrene skeleton) and carbon 5 of the isobenzofuranyl moiety of the fluorescein fluorophore; by a covalent linking moiety L, wherein the (preferably non-fluorescent) hydrophobic ester form of the fluorescein allow the penetration of the dye into the cell, wherein after cleavage by cellular esterases, in the absence of quenching metal ions the dye becomes highly fluorescent. It has been found by the present inventors that in the cells expressing functional ABC multidrug transporters, in particular ABCG2, ABCB1, or ABCC1 transporters, cellular dye fluorescence became strongly reduced.

Thus, the fluorescent dye accumulation assay, preferably PG accumulation assay of the present invention is a new, unique tool for the parallel determination of the function of the ABC multidrug transporters, in particular ABCG2, ABCB1, and ABCC1 multidrug transporters, transporting the dyes according to the present invention. Preferably, the dyes, in particular a PG dyes have very low cellular toxicity. The accumulation assay also allows the selection, separation and culturing of selected cell populations expressing either of these transporters. The accumulation assay is applicable for diagnostic purposes to assess the function of these multidrug transporters in human cells.

BRIEF DESCRIPTION OF THE INVENTION

In a first aspect the invention relates to a method of assessing ABC transporter activity of an ABC multidrug transporter capable of transporting hydrophobic or amphipathic heterocycles in a biological specimen, said method comprising the steps of:

(a) exposing a population of cells of a biological specimen, i.e. specimen cells, and optionally a population of negative control cells (or one or more population(s) of negative control cells) with a control ABC transporter activity level (i.e. from which said ABC transporter activity is missing or when a control has sufficiently lower level of the ABC transporter activity, i.e. an ABC transporter activity below a threshold level or a baseline ABC transporter activity), to a fluorescein derivative ester compound of general formula (Ia) to load the cells with said ester derivative compound in a loading medium, wherein said ester compound can be hydrolyzed to the corresponding fluorescein derivative hydroxy-compound by cellular esterases inside said cells;

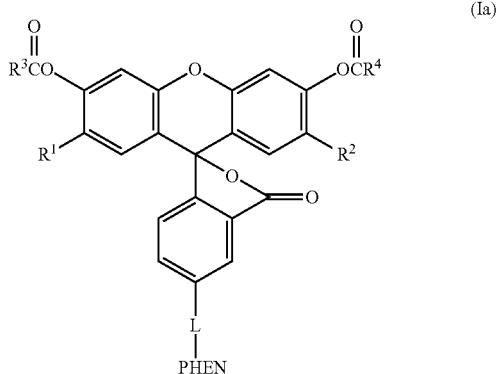

(Ia)

wherein
- $R^1$ and $R^2$ are independently selected from a group consisting of hydrogen, halogens and pseudo-halogens, preferably of H, F, Cl and Br, more preferably of H and Cl or of Cl and F; in a preferred embodiment $R^1$ and $R^2$ being identical,
- $R^3$ and $R^4$ are independently methyl, ethyl or propyl, preferably methyl or ethyl, highly preferably methyl, wherein preferably $R^3$ and $R^4$ are identical,
- L is a linker having 2 to 5 chain atoms selected from C and N, preferably said linker forming a conjugated pi electron system with both pi electrons of the fluorescein moiety and of the PHE moiety, and/or said L is selected from aminocarbonyl (carboxamide), urea, thiourea, alkenyl, C2- or C4 alkenylamine and C3 alkenylamide, preferably selected from aminocarbonyl (carboxamide), urea and thiourea,
- PHEN is a phenantrene derivative comprising 1, 2 or 3 ring nitrogens, preferably 2 ring nitrogens, in any of positions 1 to 8 of the phenantrene skeleton wherein L is covalently bound to PHEN in a position corresponding to positions 9 or 10 of the phenantrene skeleton, and (b) assessing the level of the fluorescein derivative compound (either the ester or the hydroxyl form or both) accumulating in specimen cells to obtain a level of the fluorescein derivative compound in specimen cells and optionally also in the population of negative control cells to obtain a negative control level of the fluorescein derivative compound, by an appropriate assessing method preferably by assessing the level of fluorescence in the cells, (c) comparing the level of the fluorescein derivative compound in specimen cells with a negative control level typical of missing ABC transporter activity, optionally obtained from the negative control cells (e.g. HeLa), (d) wherein a lower level of the fluorescein derivative compound in specimen cells relative to the negative control level indicates the presence and/or the level of ABC transporter activity in said biological specimen.

Preferably, the level of the fluorescein derivative compound (either the ester or the hydroxyl form or both) accumulating in specimen cells to obtain a level of the fluorescein derivative compound in specimen cells, obtained from a human subject, for determination of the function of ABC transporter activity in a given cell type is assessed.

In an embodiment the negative control level is a predetermined level, preferably pre-determined by using negative control cells.

In a preferred embodiment the ABC multidrug transporter is a multidrug transporter of the B, C or G families of ABC transporters, preferably capable of extruding a PhenGreen compound from the cells.

More preferably, the ABC multidrug transporter is selected from the group consisting of ABCB1 ($MDR^1$, Pgp), ABCC1 (MRP1) and ABCG2 (BCRP).

In a preferred embodiment the fluorescein derivative ester compound is a compound having general formula (Ib)

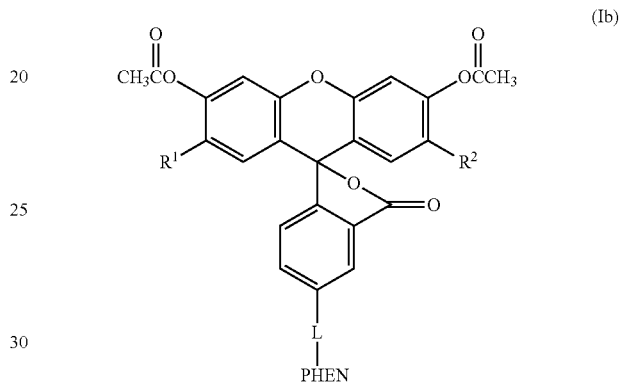

(Ib)

wherein the linker L is selected from aminocarbonyl (carboxamide), urea, thiourea, C2-alkenylamine and C3-alkenylamide, preferably from aminocarbonyl (carboxamide), urea and thiourea,
and
$R^1$ and $R^2$ are independently selected from H, F, Cl and Br, more preferably from H and Cl or from Cl and F; in a preferred embodiment $R^1$ and $R^2$ are identical,
and PHEN is as defined above.

In a highly preferred embodiment the fluorescein derivative ester compound is a compound having general formula (IIa)

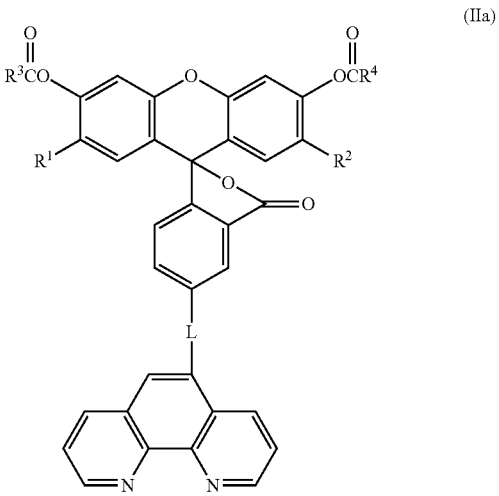

(IIa)

wherein $R^1$, $R^2$ and L are as defined above, wherein preferably
the linker L is selected from aminocarbonyl (carboxamide), urea and thiourea,
and
$R^1$ and $R^2$ are independently selected from H, F, Cl and Br, more preferably from H and Cl or from Cl and F; in a preferred embodiment $R^1$ and $R^2$ are identical,
$R^3$ and $R^4$ are independently methyl, ethyl or propyl, preferably methyl or ethyl, highly preferably methyl, wherein preferably $R^3$ and $R^4$ are identical.

Preferably, the fluorescein derivative ester compound is a compound having general formula (IIb)

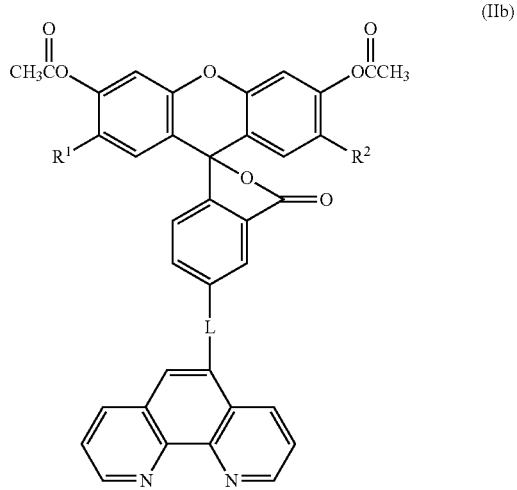

(IIb)

wherein the linker L is selected from aminocarbonyl (carboxamide), urea, thiourea, alkenyl, C2- or C4 alkenylamine and C3 alkenylamide, preferably from aminocarbonyl (carboxamide), urea and thiourea.
$R^1$ and $R^2$ are independently selected from H, F, Cl and Br, more preferably from H and Cl or from Cl and F; in a preferred embodiment $R^1$ and $R^2$ are identical,
preferably
the linker L is selected from aminocarbonyl (carboxamide), urea and thiourea,
$R^1$ and $R^2$ are independently selected from H and Cl or from Cl and F; in a preferred embodiment $R^1$ and $R^2$ are identical.

In the present invention the fluorescein derivative hydroxi compound is the corresponding alcohol after the ester groups as shown in formulae Ia, Ib, IIa and/or IIb are hydrolyzed.

Highly preferably, the fluorescein derivative ester compound is selected from PhenGreen FL diacetate and PhenGreen SK diacetate, in particular PhenGreen SK diacetate and the fluorescein derivative hydroxi compound is selected from PhenGreen FL and PhenGreen SK, PhenGreen SK, respectively.

In a preferred embodiment the biological specimen is selected from
a biological sample obtained from a multi-cellular living organism, preferably a subject, preferably a mammalian subject in particular a human subject,
a culture of cells of a multi-cellular living organism; wherein preferably the cells are mammalian cells in particular human cells.

In an alternative embodiment the multi-cellular living organism is as defined in the Definitions chapter.

In a preferred embodiment the biological specimen is a biological sample, for example a sample from blood, bone marrow, lymphatic fluid or an other body fluid comprising a population of cells expectably expressing the ABC transporter(s) of the invention or a sample obtained from a tumor; particularly preferably the sample is a blood sample. In a highly preferred embodiment populations of peripheral blood monocytes are examined.

In a further preferred embodiment a test compound is tested by the method of the present invention wherein
in step (a) or in a further step (a1) a test population of cells of the biological specimen is also exposed to a test compound (test population), wherein a reference population of cells of the biological specimen is not exposed to said test compound (reference population), wherein preferably said test compound is added to the loading buffer,
in step (b) or in a further step (b1) the level of the fluorescein derivative compound is assessed in the test population and in the reference population, to obtain the level of the fluorescein derivative compound in specimen cells of the test population and the reference population,
in step (c) or in a further step (c1) the level of the fluorescein derivative compound in specimen cells of the test population and in the reference population are also compared to each other, thereby
(e) the effect of the test compound to said ABC transporter activity is also assessed,
wherein preferably
a lower level of the fluorescein derivative compound in specimen cells of the test population relative to the level of the fluorescein derivative compound in the cells of the reference population indicates that the test compound is an activator of the ABC transporter activity in said biological specimen and/or
a lower level of the fluorescein derivative compound in the cells of the reference population relative to the level of the fluorescein derivative compound in the specimen cells of the test population indicates that the test compound is an inhibitor of the ABC transporter activity in said biological specimen.

Preferably, the test compound is selected from compounds having and intracellular effect, cytotoxic compounds and therapeutic compound, preferably chemotherapeutic compounds and compounds assumed to have such effect.

In the method according to the specification a negative control cell population is applied and the cells of the population are selected from the following types of cells:
cells which do not express the ABC transporter protein,
cells which express the ABC transporter protein under a pre-determined threshold value,
cells in which the expression of the ABC transporter protein is silenced,
cells which express a mutant ABC transporter protein which is not capable of transporting the fluorescein derivative of the invention (either in ester or in hydroxi form) and/or
cells in which the activity of the ABC transporter protein is inhibited;
preferably wherein one or more control cell populations are applied.

In a preferred variant or embodiment comparing the level of the fluorescein derivative compound in specimen cells with a negative control level comprises a quantitative assessment of ABC transporter activity.

In a preferred method of assessment a quantitative measurement and calculation is carried out.

Preferably the quantitative assessment of ABC transporter activity comprises
  expressing the level of the fluorescein derivative compound in specimen cells as quantitative value (F) and the negative control level of the fluorescein derivative compound as quantitative value (F*) and
  subtracting one of the quantitative values from the other.

Preferably, comparing the level of the fluorescein derivative compound in specimen cells with a negative control level comprises
  expressing the level of the fluorescein derivative compound in specimen cells as quantitative value (F), preferably as rate of accumulation (F) of the fluorescein derivative compound within said cells; and then
  expressing the negative control level of the fluorescein derivative compound as a quantitative value (F*), preferably as a rate of accumulation (F*) of the fluorescein derivative compound in said negative control cell, and
  calculating the MDR activity factor (MAF) that is illustrative of the measure of the activity of said ABC transport protein present in said specimen cells using the correlation: MAF=(F*−F)/F*.

Highly preferably,
  the level of the fluorescein derivative compound in specimen cells of the test population is quantitatively determined as a test MAF value and
  the level of the fluorescein derivative compound in the reference population is also quantitatively determined as a reference MAF value, and
  the effect of the test compound to said ABC transporter activity is assessed by comparison of MAF values.

In a preferred method said fluorescein derivative compound assessing method comprises fluorometry.

In a preferred method said fluorescein derivative compound assessing method comprises flow cytometry.

In a preferred method said fluorescein derivative compound assessing method comprises cell imaging, e.g. fluorescence microscopy.

In a preferred embodiment of the method of the invention said method further comprising one or more of the following steps:
  measuring the survival of cells in said specimen,
  determining the amount of a multi-drug transporter protein made by said specimen cells,
  determining the amount of a multi-drug transporter protein on the surface of said specimen cells.

In a preferred variant the survival of cells in said specimen is detected by
  staining of live cells by antibody,
  staining of dead cells with an appropriate dye.

There is also provided herein a diagnostic assay in which the sample is obtained from a subject who is assumed to have a condition characterized by an altered activity or expression of one or more of the ABC transporters of the invention.

According to the invention any of the above method which is a diagnostic method or which is carried out as a diagnostic method.

Thus, the invention relates to any one of the above defined methods in a diagnostic method.

In a preferred embodiment the sample is obtained from a biological fluid comprising cells which are typically overexpress one or more of the ABC transporters of the invention.

In a preferred embodiment the biological specimen is a biological sample obtained from a mammalian subject, preferably a human subject, and the level of the fluorescein derivative compound accumulating cells of the biological sample, i.e. sample cells is assessed and thereby the ABC transporter activity is assessed in said sample cells.

In a preferred embodiment the biological sample is a blood sample or a bone marrow sample. In a preferred embodiment flow cytometry measurement is carried out and the population of blood cells are differentiated or separated or measured separately.

In a preferred embodiment a chelator is applied to bind metal ions. In an embodiment the chelator is EDTA.

In a preferred embodiment the fluorescein derivative compound of the invention is non-toxic to the cells or used in a non-toxic concentration. Preferably the transporter activity is assessed in living cells. Preferably cell survival is assessed as given above.

Preferably, in the method, use of kit according to any of the previous claims wherein the concentration of the fluoresceind derivative compound, preferably PGD is 0.1-3 µM, preferably 0.1-2 µM, more preferably 0.2-0.8 µM, highly preferably 0.3-0.7 µM.

In an embodiment the diagnostic method, wherein the mammalian subject is a patient to be diagnosed for a condition wherein transport activity of the ABC multidrug transporter capable of transporting hydrophobic heterocycles is altered or modulated in a population of cells of said patient, wherein
  the ABC transporter activity is assessed in said sample cells, and
  said ABC transporter activity is compared with a normal ABC transporter activity level in healthy subjects,
  and wherein the ABC transporter activity level is altered or modulated in the sample cells in comparison with the normal ABC transporter activity level, the altered or modulated level in said patient is considered as indicative of said condition.

In an embodiment the normal ABC transporter activity level is given as a range.

Preferably the range is obtained by measuring ABC transporter activity in a plurality or cohort of healthy subjects and a normal range is defined by statistical distribution of the measured data.

In an embodiment said condition is a condition which can be treated by a treatment specific for said condition, and wherein the altered or modulated level of the ABC transporter in said patient indicates that said patient is in need of said treatment.

In an embodiment the condition is a disease wherein one or more of the ABC transporters is/are upregulated or their activity is increased.

In an embodiment the condition is a disease wherein one or more of the ABC transporters is/are downregulated or their activity is decreased.

In an embodiment a pattern of multiple ABC transporter activities are measured by using specific inhibitors selected from specific inhibitors of a multidrug transporter of the B, C or G families of APC transporters, which are preferably capable of extruding a PhenGreen compound from the cells.

More preferably, a pattern of multiple ABC transporter activities are measured by using specific inhibitors selected from specific inhibitors of an ABC multidrug transporter selected from the group consisting of ABCB1 (MDR[1], Pgp), ABCC1 (MRP1) and ABCG2 (BCRP).

In a preferred embodiment said biological sample is a blood sample, a blood derived sample, e.g. a cellular fraction of blood, or a sample comprising immune cells, e.g. a lymphatic fluid sample, a biopsy sample, e.g. a bone marrow sample or a sample from a tumor tissue.

In a particularly embodiment the sample is a blood sample. In a highly preferred embodiment populations of peripheral blood monocytes are examined.

The sample comprises a population of cells expectably expressing the ABC transporter(s) of the invention or a sample obtained from a tumor.

In a preferred embodiment said condition is a condition wherein said ABC transporter is overexpressed, preferably cancer disease or an immunological disease.

In a preferred embodiment of the diagnostic method the level of the ABC transporter activity in sample cells is quantitatively determined by obtaining a patient MAF value and the level of the normal level is also quantitatively expressed as a normal MAF value or MAF range, and wherein the ABC transporter activity level altered or modulated in the sample cells is determined by comparison of the patient MAF value with the normal MAF value or MAF range.

Preferably the normal MAF value or MAF range is obtained by carrying of the method of the invention in biological samples from one or more healthy patients as explained above.

In a further preferred embodiment a test compound is tested within the diagnostic method of the present invention to assess the effectiveness of the test compound for treatment of the patient. In a particular embodiment the test compound is tested by the method as defined above. Preferably the test compound is a medicament or a candidate drug.

In a preferred embodiment said diagnostic method is carried out multiple times to monitor the condition in said patient.

In a further preferred embodiment the patient is a patient suffering in a disease characterized by altered ABC transporter activity eg. multidrug resistance. In an embodiment the patient is under treatment of said disease and said diagnostic method is carried out multiple times to monitor the effectiveness treatment, preferably at pre-defined times required by a treatment protocol.

In an embodiment if diagnosis indicates that the patient is in a condition to be treated or in a condition to be treated differently from previous treatment, the patient is treated differently.

In a further aspect of the invention there are provided uses, preferably corresponding to, mutatis mutandis, the methods specified above.

The invention relates to a use of a fluorescein derivative compound as defined above for assessing ABC transporter activity in a biological specimen. In this regard, optionally, the appropriate method defined above can be reformulated as a use.

The invention relates to a use of a fluorescein derivative compound as defined above for testing a test compound for its effect on ABC transporter activity in a biological specimen. The invention relates to a use of a fluorescein derivative compound as defined above and that of a test compound for testing said test compound for its effect on ABC transporter activity in a biological specimen. In this regard, optionally, the appropriate method defined above wherein a test compound is tested can be reformulated as a use.

The invention relates to a use of a fluorescein derivative compound as defined above for the selection of cells having or not having the ABC transporter activity as measured according to any of the methods as defined above in a biological specimen.

The invention relates to a use of a fluorescein derivative compound as defined above for the diagnostic measurement of the the ABC transporter activity in a given cell type. Preferably the measurement is carried out according to any of the methods as defined above in a biological specimen, preferably a biological sample.

Preferably, the diagnostic method is for diagnosing a patient a condition wherein transport activity of the ABC multidrug transporter capable of transporting hydrophobic or amphipathic heterocycles is altered or modulated in a population of cells of said patient, i.e. sample cells, especially for diagnostic purposes to obtain quantitative activity values for the given ABC transporters in a given cell type.

Preferably, the mammalian subject is a patient to be diagnosed for a condition wherein the transport activity of the ABC multidrug transporter capable of transporting hydrophobic or amphipathic heterocycles is increased in a population of cells of said patient, or
is decreased in a population of cells of said patient.

The diagnostic use or method according to any of the previous claims wherein the biological sample when the fluorescent derivative compound is added, is a metal-free medium, and/or
comprises a metal-chelator,
in particular EDTA, in particular wherein PHE is a metal chelator, preferably 1,10 phenantrene.

In a preferred embodiment of the diagnostic method or use the concentration of PGD is 0.1-3 µM, preferably 0.1-2 µM, more preferably 0.2-0.8 µM, highly preferably 0.3-0.7 µM.

In a further aspect the invention relates to a kit for assessing ABC transporter activity in a biological specimen, said kit comprising a fluorescein derivative compound as defined above,
a loading buffer,
and optionally
negative control cells and or
an inhibitor of the ABC transporter activity
means to detect PhenGreen
and instructions for detecting multi-drug resistance in a biological specimen.

In a preferred embodiment the invention relates to the use of said kit for any of the uses as defined above or in any of the methods as defined above.

Preferably, in the method, use of kit according to any of the previous claims wherein the loading buffer is a metal-free medium, and/or
comprises a metal-chelator,
in particular EDTA, in particular wherein PHE is a metal chelator, preferably 1,10 phenantrene.

In particular such loading buffer is applied when PHE is phenantroline or any metal chelating derivative thereof.

Preferably the medium or the kit comprises a sugar source, in particular glucose.

Preferably, in the method, use of kit according to any of the previous claims wherein the concentration of PGD is 0.1-3 µM, preferably 0.1-2 µM, more preferably 0.2-0.8 µM, highly preferably 0.3-0.7 µM.

Definitions

A "membrane transporter" as understood herein is a cell membrane integrated protein which is capable of transporting, e.g. exporting (extruding) or importing entities, in the present context molecules, either actively or passively through the membrane into which it is integrated in.

"ABC transporter" as used herein stands for ATP-binding cassette transporters which are a superfamily of membrane transporters that utilize the energy of adenosine triphosphate (ATP) hydrolysis to carry out biological processes, in case of ABC transporters processes including transport of entities in the context of the present invention molecules, across membranes. Denominations and subfamilies of ABC transporters are used herein as assigned by the HUGO Gene Nomenclature Committee (HGNC).

For example, membrane transporters of the "ABCG family" belong to the G subfamily of ABC transporters consisting of half-transporters, which oligomerise to form the functional transporter. ABCG2 (other names among others: BRCP, MXR[1], CDw338) is a multidrug transporter member of the family.

Membrane transporters of the "ABCB family" belong to the B subfamily of ABC transporters, which comprises both full transporters and half transporters which is unique among the ABC transporter families. ABCB1 (MDR[1], Pgp) is overexpressed in certain tumor cells which protein exhibit multi-drug resistance. Normally it is expressed in the blood brain barrier and liver.

Membrane transporters of the "ABCC family" belong to the C subfamily of ABC transporters. This is a large family which contains thirteen members to our present knowledge among which nine are Multidrug Resistance Proteins (MRPs) which are multi-drug transporters. The MRP proteins are found throughout nature and they mediate many important functions.

Preferably, the ABC transporter proteins according to the invention are multidrug transporters.

A "multidrug transporter" is an ABC transporter protein, also mentioned herein as an ABC multidrug transporter, which can extrude from the cell in the membrane of which the ABC transporter protein is present, a multiplicity or preferably a wide variety of chemical compounds which are chemically unrelated i.e. have no evident (prima facie) structural similarity or relationship.

In a preferred embodiment the ABC multidrug transporter is a multidrug transporter capable of transporting (extruding i.e. transporting form the cell to the extracellular space) hydrophobic compounds, preferably hydrophobic heterocycles (i.e. an ABC multidrug transporter capable of transporting hydrophobic heterocycles).

A multidrug transporter is typically an ABC transporter which causes multidrug resistance in a cell, typically in a cancer cell.

In a particular embodiment the ABC multidrug transporter is capable of transporting compounds consisting of a fluorescein derivative and a phenantrene derivative (preferably phenantroline) linked via a linker as defined herein, preferably PhenGreen. The latter activity is called PhenGreen-transporting activity. In a highly preferred embodiment PhenGreen is selected from the group consisting of Phen-Green FL diacetate and PhenGreen SK diacetate and as present in the cells as a major compound, PhenGreen FL and PhenGreen SK, in particular PhenGreen SK diacetate and PhenGreen SK, respectively.

More information can be found on ABC transporters in Alexander S P H, Kelly E, Marion N, Peters J A, Benson H E, Faccenda E, Pawson A J, Sharman J L, Southan C, Davies J A and CGTP Collaborators (2015) The Concise Guide to PHARMACOLOGY 2015/16: Transporters. Br J Pharmacol. 172: 6110-6202.

An ABC transporter according to the present invention may be an ABC transporter from e.g. a multi-cellular plant or animal. In a preferred embodiment the animal is an anthropod, e.g. an insect or, preferably, a vertebrate animal, e.g. a fish, an amphibian, reptile, a bird or a mammal. In a more preferred embodiment the animal is a mammal, in a highly preferred embodiment is a human. The plant is typically a monocotyledon or a dicotyledon. In a preferred embodiment the ABC transporter is a homologue of MDR[1], MXR (BCRP) or MRP, or of ABCB1, ABCC1 or ABCG2 in the given organism or a transporter of a corresponding or closest gene which is capable of extruding the fluorescent compound of the invention. ABC transporter according to the present invention include functional mutants have an at least 70%, 80%, 90%, 95% sequence identity providing that the active site and transporter activity is maintained.

"ABC transporter activity", i.e. the "activity" of an ABC transporter protein refers to any activity exerted by the said transporter protein including e.g. its biological function, transport activity, i.e. transport of a drug through the membrane carrying the said protein, or ATP-ase activity, as far as it is an indicator of transport activity, like substrate stimulated ATP-ase activity. In a broad sense, "activity", from the point of view of detection of transport activity, may cover herein any partial reaction (e.g. substrate binding) of the whole reaction cycle of the enzyme as far as transport occurs and it can be detected, assessed or measured in the conditions given via the partial activity.

A negative control level is understood herein as an ABC activity level wherein the ABC transporter activity to be assessed or measure is considered as missing (level typical of missing ABC transporter activity). This may be assessed or measured when a negative control cell population is applied and in a particular embodiment the cells of the population are selected from the following types of cells:
  cells which do not express the ABC transporter protein,
  cells which express the ABC transporter protein under a pre-determined threshold value,
  cells in which the expression of the ABC transporter protein is silenced,
  cells which express a mutant ABC transporter protein which is not capable of transporting the fluorescein derivative of the invention (either in ester or in hydroxi form) and/or
  cells in which the activity of the ABC transporter protein is inhibited.

Thus, the negative control level is a reference level used to calculate the value typical of the ABC activity level given. It follows that the "missing ABC transporter activity" is a consideration for the measurement and is to be understood that it is considered as missing in the method given.

A "substrate" of an ABC transporter protein is a compound that can be extruded from the cell through an ABC transporter mediated active transport mechanism.

An "activator" substance increases activity as defined herein, whereas an "inhibitor" substance decreases activity of the said ABC multidrug transporter. An inhibitor can be, for example, an inhibitor of the transport process or a good substrate of same applied in excess of the amount of the compound of interest present (competitive inhibitor).

A "biological specimen" as used herein is a biological sample or a biological culture comprising cells in which the ABC transporter activity is or is to be examined or assessed.

The term "biological sample" refers to a composition of matter or materials comprising cells, said composition has been obtained from an environment, typically from a living organism or an ecosystem (an environment comprising living organisms), preferably an organism, including compositions which are processed e.g. completed with appropriate agents and/or cultured from the originally collected sample.

A "diagnostic sample" as used herein is a biological sample obtained from an animal, preferably a mammalian or a human comprising cells in which the ABC transporter activity is or is to be examined or assessed for diagnostic purposes. A "biological culture" or "culture" is a composition of matter or materials comprising cells, optionally in the form of tissues, wherein the cells are placed in a medium or under conditions suitable to maintain at least a part or subpopulation of them in a viable form; optionally in a medium or under conditions wherein the cell are capable of propagating.

In quite usual cases a "biological culture" is also a biological sample, if at least the cells or a part or subpopulation of the cells have been previously obtained from the environment, e.g. from a living organism or an ecosystem, and then transformed into a culture.

The living organism, from which the sample is taken is preferably a multi-cellular plant or animal. In a preferred embodiment the animal is an anthropod, e.g. an insect or, preferably, a vertebrate animal, e.g. a fish, an amphibian, reptile, a bird or a mammal. In a more preferred embodiment the animal is a mammal, in a highly preferred embodiment is a human. The plant is typically an economically important plant for example those listed in [Bennett, B. C. 2007. Chapter 3. Twenty-five Important Plant Families. B. C. Bennett, editor. UNESCO Encyclopedia of Life Support Systems. eolss.net.] but not limited thereto.

The "biological sample" may be obtained from tissue, bodily fluid, or microorganisms collected from a subject. In case of vertebrates sample sources include, but are not limited to, sputum (processed or unprocessed), bronchial alveolar lavage (BAL), bronchial wash (BW), blood, whole blood, bodily fluids, cerebrospinal fluid (CSF), lymphatic fluid, urine, plasma, serum, provided that it comprises cells, or a tissue (e.g., biopsy material).

A test specimen or sample, or a diagnostic sample is one in which the cells, in which said ABC transporter activity to be assessed is present. A control specimen may be a control sample or a control culture in which control cells are present. Control cell may be positive control cells with a known or pre-determined level, preferably high level of ABC transporter activity. High level is understood that it is in the upper range of the expected measurement range. Negative control cells are cells from which said ABC transporter activity is missing cells having an ABC transporter activity below a threshold level or having a baseline ABC transporter activity. Preferably the threshold level and/or the baseline level is pre-determined in previous experiment or set to a value which is in the lower range of the expected measurement range.

"Assessing" a value e.g. a level of a compound is understood herein to cover quantitative of even analytically precise determinations, preferably from multiple samples, including calculations and optionally also statistical analysis and to cover less precise determination, e.g. quantitative determination without statistical analysis or semi-quantitative determinations or even determinations with a few result values (e.g. low, medium, high or yes or no/present or not present). Preferably assessing means quantitative determination or measurement with calculation, i.e. "Measuring". In the present invention preferably the level of activity, preferably transport activity of an ABC transporter protein is assessed or measured.

"Comparing" two levels is understood herein to include a comparison to establish which is higher or lower, or establishing a difference or establishing a ratio of the levels, or values derived from the levels, optionally completed with other mathematical procedures as the assessment (calculation) method requires.

"Significant" is to be understood herein as statistically significant according to any statistical hypothesis testing method appropriate in the given assay method, preferably in the field of fluorescent spectroscopy, measurement of fluorescent in cells, flow cytometry, membrane transport activity measurement, and the like. The skilled person is familiar with statistical hypothesis testing methods. A "significant difference" between two sets of measured values or between a measured value and a set of measured values defining a range (e.g. as a confidence interval) is understood as a statistically significant difference. Preferably, in this case a hypothesis that there is no relationship between two sets of values or between the value and the set of values cannot be rejected based on the given statistical method applied.

A "subject" is an animal or preferably mammalian or human individual.

A "patient" is a subject under medical care, preferably observation, diagnosis, treatment of prevention.

A patient may be healthy or may suffer in a disease.

A "condition" is a purposive selection of features of a subject or a group of subject. A condition may describe the state or status of said subject. A condition may be for example a disorder or disease or set of symptoms, a healthy status or a genetic feature or a phenotype.

A "typical range" or a "regular range" of values measured in connection with a cohort or a population of subjects is a range of values typical for the majority of subject or for a subgroup of subjects sharing a common feature wherein said subgroup comprises the majority of the subjects in said cohort or population.

A "normal range" of values measured in connection with a cohort or a population of subjects is a range of values having some or any advantage for subjects characterized thereby over values falling outside the range and being typical for other subjects. Preferably a "normal range" is a range of values typical of healthy subjects.

A "normal level" is a normal range which is relatively narrow or a single value. In a broader sense normal range and normal level are used interchangeably.

A "normal condition" of a subject is a condition having some or any advantage for said subject over other condition characteristic to other subjects.

As used herein the singular forms "a", "an" and if context allows "the" include plural forms as well unless the context dictates otherwise. Thus the meaning of "a" or "an" if the context allows includes the meaning "one or more".

"Isolated" means altered "by the hand of man" from the natural state. If a molecule or composition occurs in nature, it has been "isolated" if it has been changed and/or removed from its original environment.

The term "comprises" or "comprising" or "including" are to be construed here as having a non-exhaustive meaning and allow the addition or involvement of further features or method steps or components to anything which comprises the listed features or method steps or components.

The expression "consisting essentially of" or "comprising substantially" is to be understood as consisting of mandatory features or method steps or components listed in a list e.g. in a claim whereas allowing to contain additionally other features or method steps or components which do not materially affect the essential characteristics of the use, method, composition or other subject matter. It is to be understood that "comprises" or "comprising" or "including" can be replaced herein by "consisting essentially of" or "comprising substantially" if so required without addition of new matter.

Selection from a list, for example the term "selected from" can be replaced by "selected from a group consisting of" if practice so requires and, if context allows, includes selecting one or more item(s) from the list.

Panel A. Control PLB cells and ABCB1-expressing PLB cells, Panel B. Control A431 cells and ABCB1-expressing A431 cells, Panel C. Control HL-60 cells and ABCC1-expressing HL-60 cells, Panel D. Control HEK cells and ABCC1-expressing HEK cells.

Panel E. Control PLB cells and ABCB1-expressing PLB cells, Control A431 cells and ABCB1-expressing A431 cells Panel F. Control HL-60 cells and ABCC1-expressing HL-60 cells, Control HEK cells and ABCC1-expressing HEK cells.

Figure 6:
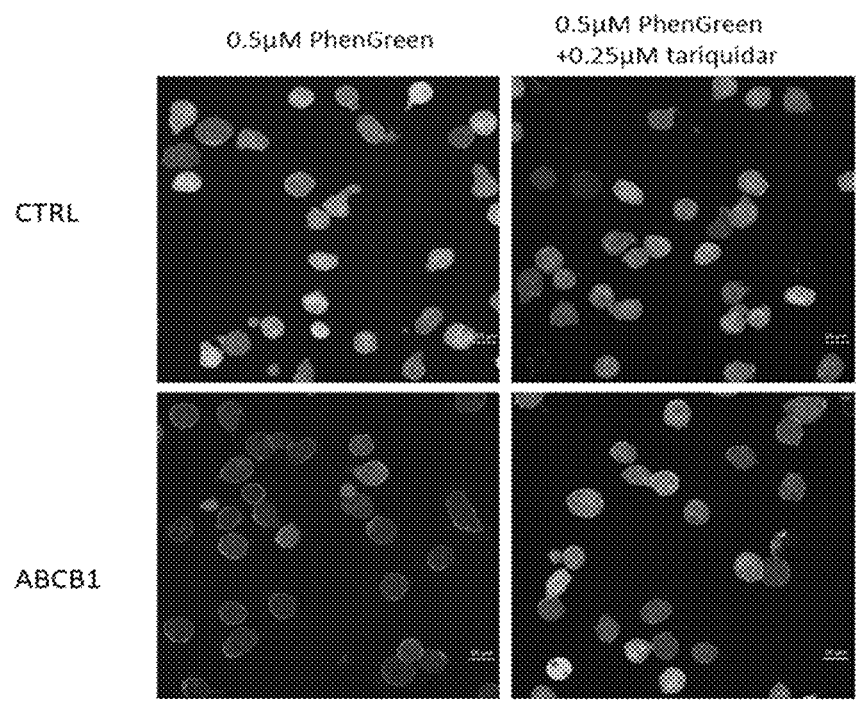
Figure 6:
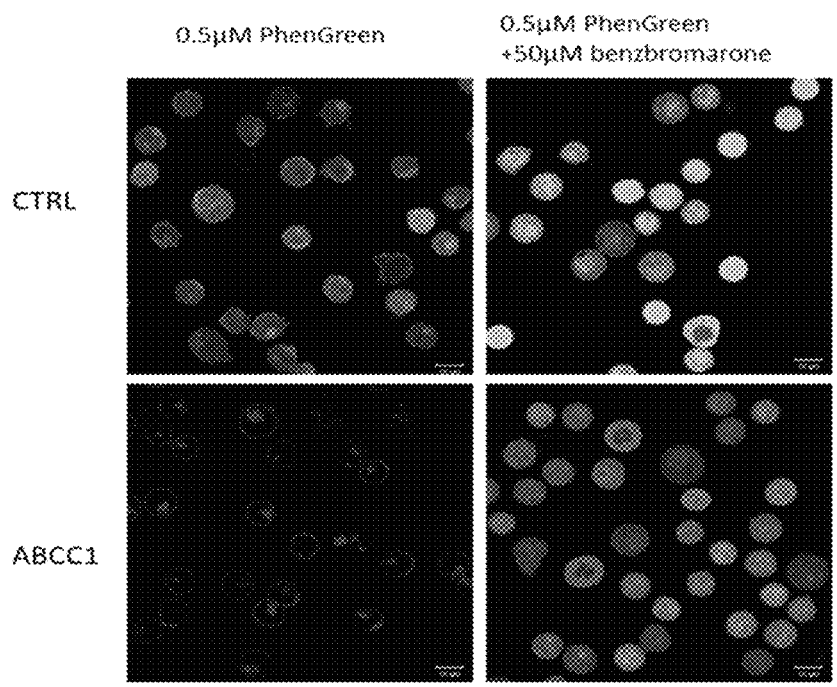

FIG. 6. Fluorescent PG accumulation in human PLB and HL-60 cells, examined by confocal microscopy. Effects of ABCB1 and ABCC1 protein expression and the specific inhibition of the transporter function by tariquidar (ABCB1) or by benzbromarone (ABCC1). PG fluorescence examined after 30 minutes of the addition of 0.5 μM PGD to the medium, either in the absence or presence of the transporter inhibitors (0.25 μM tariquidar for ABCB1 or 50 μM benzbromarone for ABCC1) in cells pre-labeled with fluorescent anti-WGA to indicate the plasma membranes.

Figure 7:
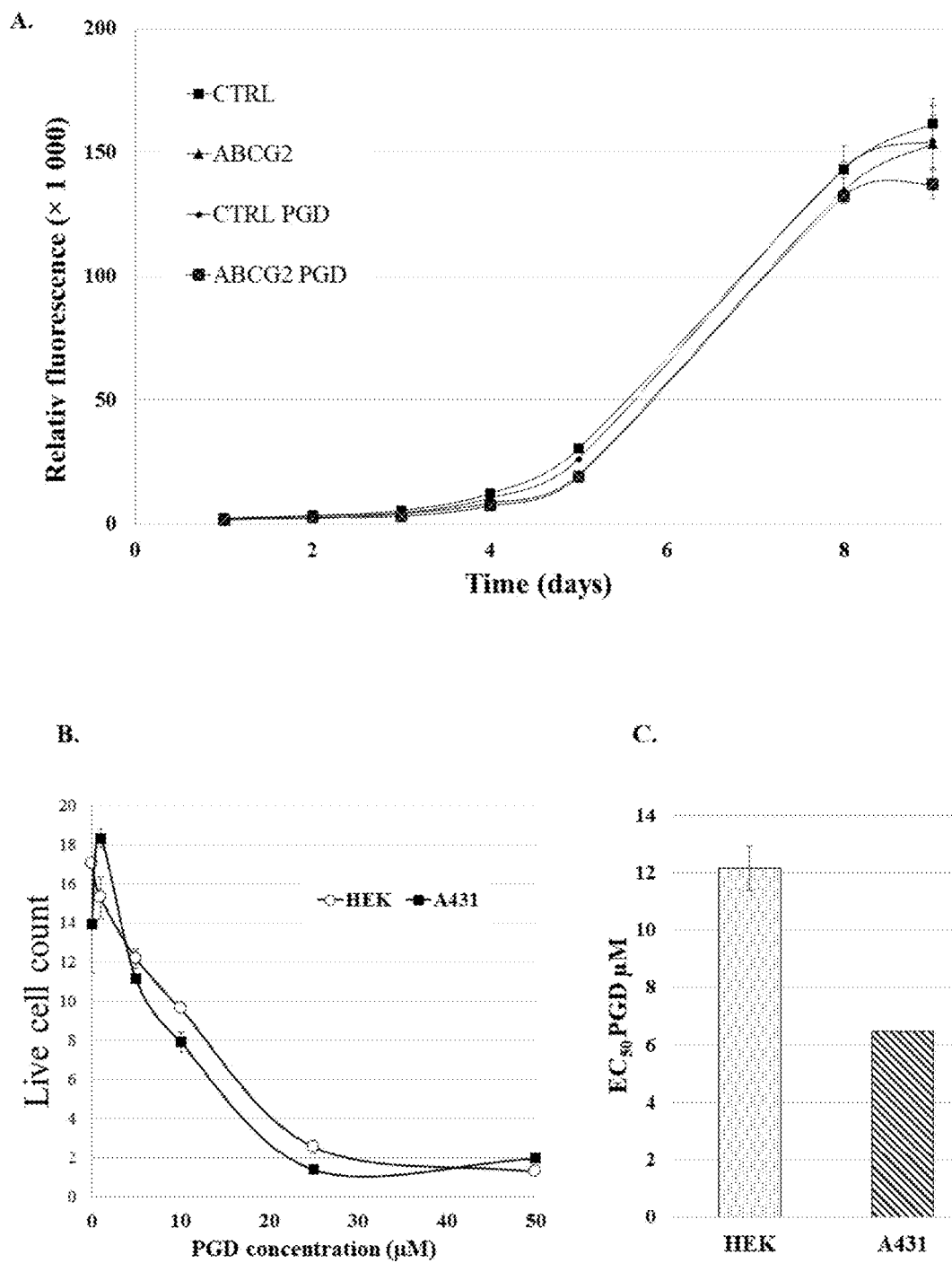

FIG. 7. PhenGreen diacetate toxicity assay. Panel A. Effect of PhenGreen accumulation on cell growth in PLB cells and PLB-ABCG2 cell. Cell growth was measured after 0.5 μM PGD treatment for 30 minutes at 37° C., followed by cell sorting. Panels B and C. Cytotoxic effects of PGD treatment in HEK and A431 cells. The cells were pre-treated with the indicated concentrations of PGD for 30 min at 37° C. in the loading media, then washed and cultured in normal cell culturing media (see Methods) for 72 hours.

Figure 8:
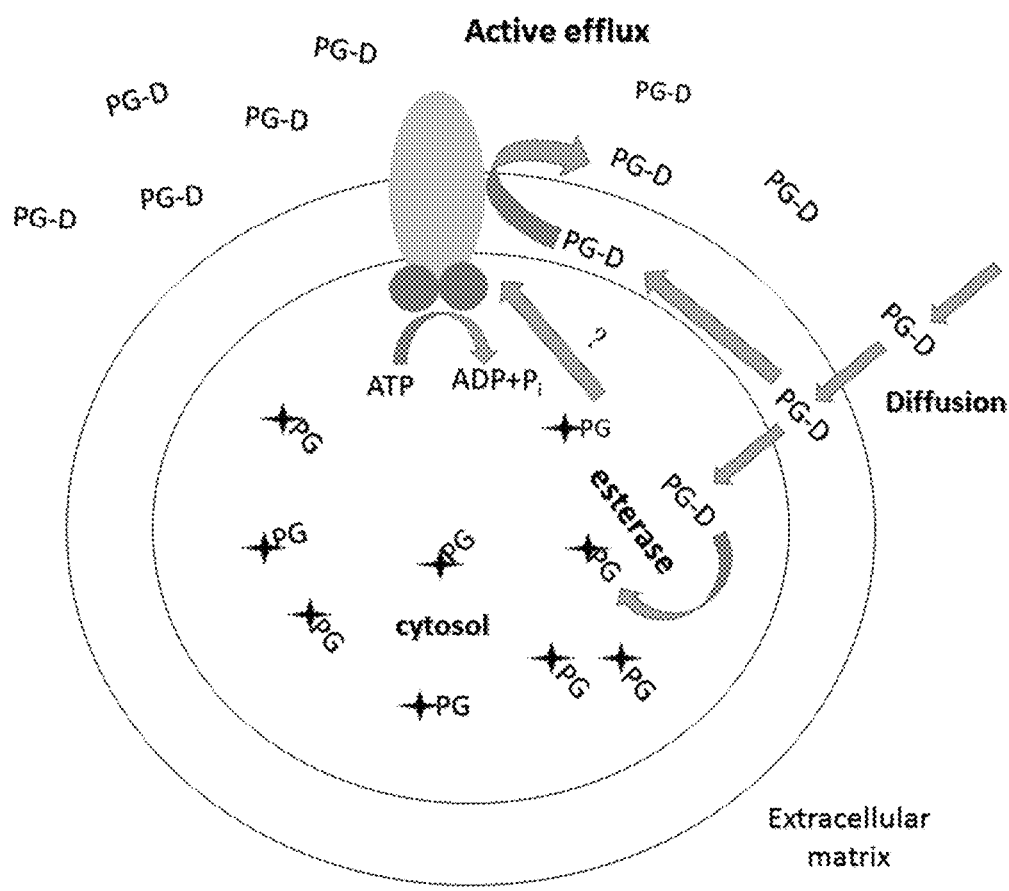

FIG. 8. An illustration of the functional presence of ABCG2, ABCB1 and ABCC1 is capable to reduce PG accumulation.

FIG. 9A. Western blot anti-ABCG2 (BXP-21) staining, and flow cytometry anti-ABCG2 (5D3) immunofluorescent staining of ABCG2 in human PLB cells—control PLB and PLB-ABCG2 cells FIG. 9B. Western blot anti-ABCG2 (BXP-21) staining, and flow cytometry anti-ABCG2 (5D3) immunofluorescent staining of ABCG2 in human A431 cells—control A431 and A431-ABCG2 cells.

FIG. 10A. Western blot anti-ABCB1 (C219) staining, and flow cytometry anti-ABCB1 (MRK16) immunofluorescent staining of ABCB1 in human PLB cells—control PLB and PLB-ABCB1 cells FIG. 10B. Western blot anti-ABCB1 (C219) staining, and flow cytometry anti-ABCB1 (MRK16) immunofluorescent staining of ABCB1 in human A431 cells—control A431 and A431-ABCB1 cells FIG. 11A. Western blot anti-ABCC1 (MRPm6) staining, and flow cytometry anti-ABCC1 (QCRL3) immunofluorescent staining of ABCC1 in human HL60 cells—control HL60 cells and HL60-ABCC1 cells FIG. 11B. Western blot anti-ABCC1 (MRPm6) staining, and flow cytometry anti-ABCC1 (QCRL3) immunofluorescent staining of ABCC1 in human HEK cells—control HEK cells and HEK-ABCC1

Figure 12:
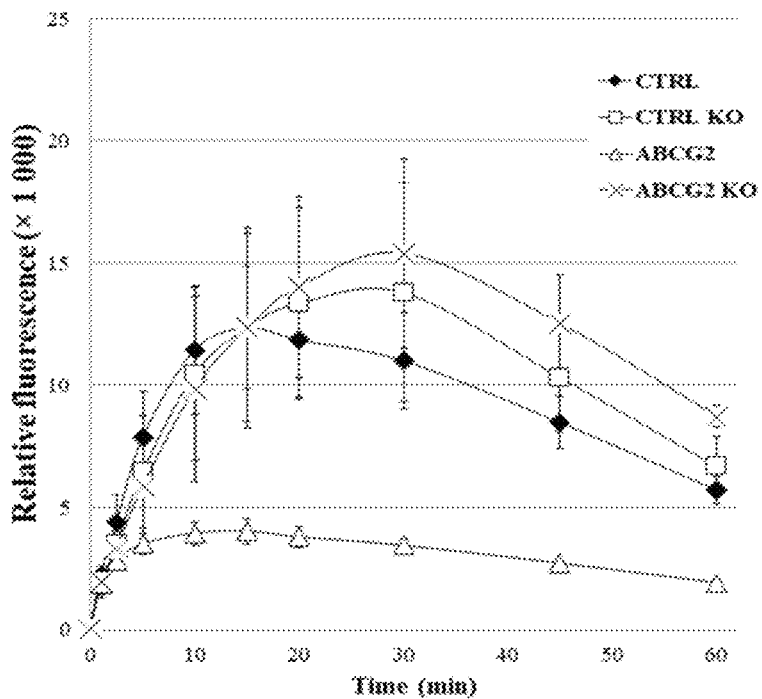
Figure 12:
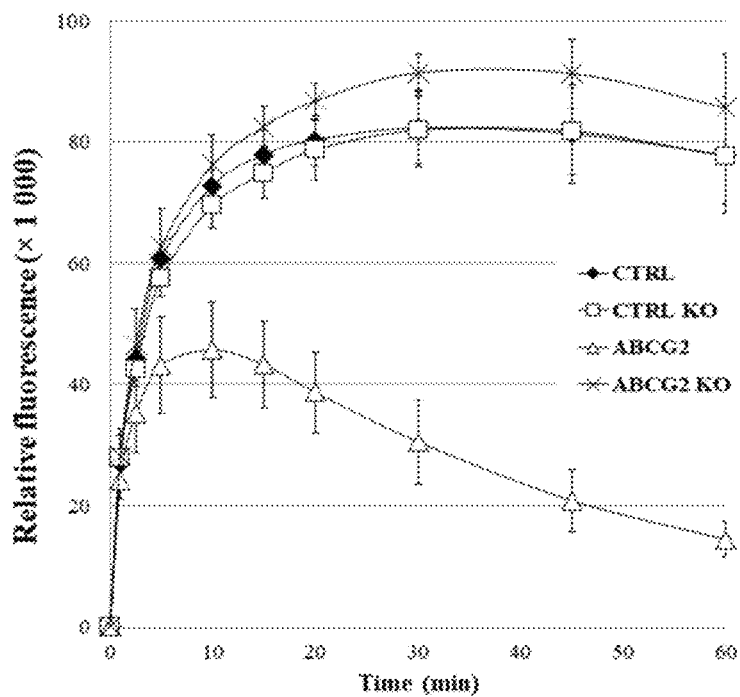

FIG. 12. Time dependence of PhenGreen accumulation in human PLB cells and in PLB cells expressing ABCG2. Effect of the ABCG2 inhibitor Ko143. Panel A: PG accumulation in the presence of 0.5 μM PGD, Panel B: PG accumulation in the presence of 2.5 μM PGD in the loading media.

Figure 13:
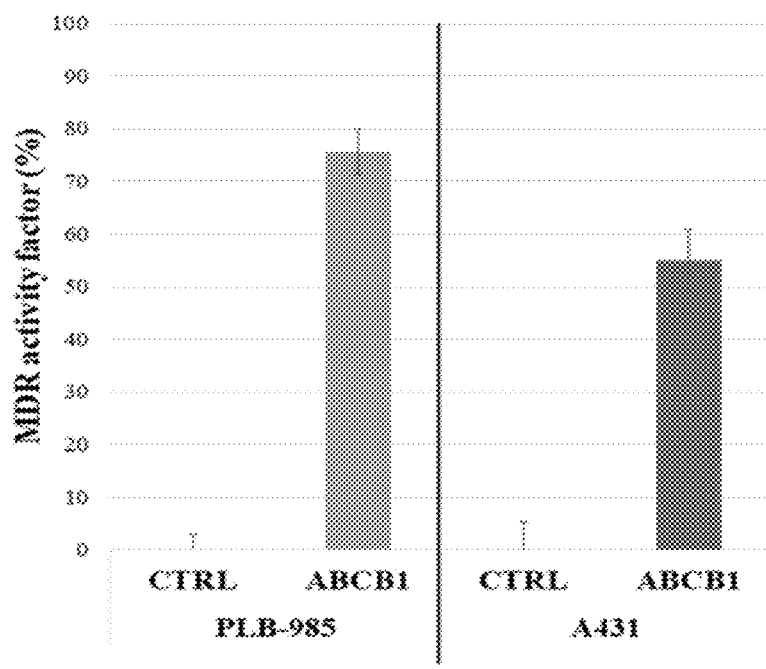
Figure 13:
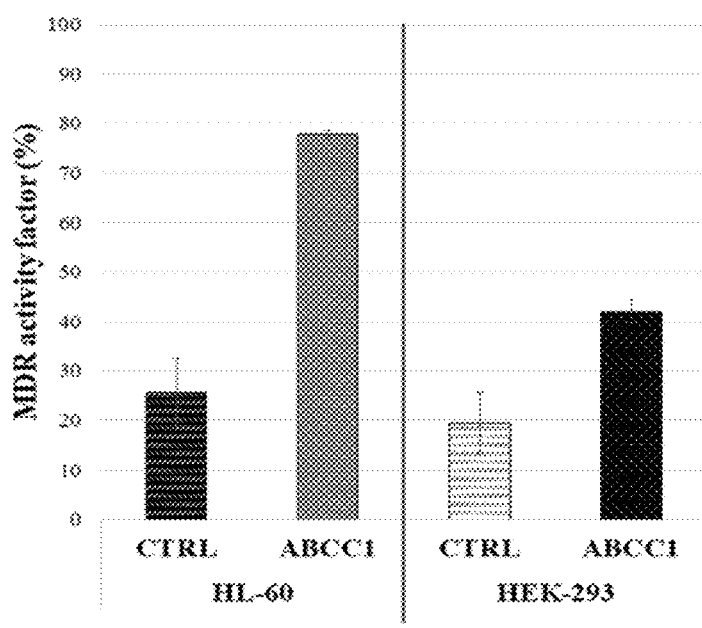

FIG. 13. MDR activity factor measurements based on mitoxantrone (MX) accumulation in various cell lines expressing ABCB1 or ABCC1 transporter. MX accumulation was measured in the indicated cell lines in the presence of 1 μM MX, for 60 min at 37° C.

FIG. 14.

Structure of PhenGreen diacetate and the product after esterase activity.

FIG. 15.

Functional test in human peripheral blood mononuclear cells (PBMCs) by PGD, CaAM or Mx with or without transporter inhibitors. Panel A. is a representative figure of mononuclear cell populations as visualized by flow cytometry. Panel B. shows the flow cytometry measurements based on Phengreen (PG), Calcein (CaAM) and Mitoxantrone (Mx) uptake for the three ABC transporters studies, and in the three respective leukocyte populations. Panel C. MDR activity factors (calculated as described above) are shown based on the measurements of the accumulation of the three fluorescent dyes, with or without inhibitors, in the respective leukocyte populations.

DETAILED DESCRIPTION OF THE INVENTION

In the description the inventors document that the application of PhenGreen SK diacetate (PGD) allowed a parallel and sensitive functional detection of all these three major ABC multidrug transporters. PGD is a non-fluorescent, hydrophobic molecule, which rapidly enters the cells, where PGD is cleaved by non-specific esterases to yield a highly fluorescent hydrophilic dye, PhenGreen (PG), trapped inside the cell. The green fluorescence of PG is variably quenched in the presence of divalent metal ions, especially by heavy metal ions [Ma Y, et al. *Metallomics. Royal Society of Chemistry;* 2015]. Therefore, this PGD loading and PG fluorescence measurement technology has been applied for the determination of iron or cadmium ions in various cellular systems.

Interestingly, as shown here, PG accumulation is strongly reduced by the function of the ABCG2, ABCB1, as well as by the ABCC1 transporter. It has been documented that under appropriate assay conditions, in the absence of divalent quenching ions, fluorescent PG accumulation can be efficiently used for a functional assay of all these drug transporters. Flow cytometry and fluorescence microscopy, allowing high-throughput and high-content assays, are both suitable for performing these measurements, and short-term PG accumulation is non-toxic to the cells. Parallel application of selective transporter inhibitors make this assay a simple, versatile and sensitive tool to assess specific ABC multidrug transporter function.

Thus, in a variant of the assay one or more inhibitors specific to a single transporter is applied.

A quantitative assessment of the transporter function provides an important diagnostic tool to assess the drug-sensitivity or other features of human cellular samples in medical applications.

It can be contemplated from the experiments that in case of multidrug transporters other highly similar dyes will be extruded analogously and with similar results, as far as their cell-permeable ester form can enter the cells and once hydrolyzed within the cell can be extruded therefrom by the ABC multidrug transporter, as defined herein, in particular by the three major multidrug transporter ABCG2, ABCB1 and ABCC1.

It is contemplated that the transport function of key human ABC multidrug transporters can be assessed with a cell permeable fluorescent metal ion indicator comprising a phenantroline moiety or an analog thereof linked to a 3',6' dihydroxi fluorescein fluorophore via carbon 5 or 6 of phenantroline and carbon 5 of the isobenzofuranyl moiety by a covalent linking moiety L, wherein the (preferably non-fluorescent or having a different or differentiable fluorescent signal) hydrophobic ester form of the 3' and 6' hydroxyl groups allow the penetration of the dye into the cell, wherein after cleavage by cellular esterases, in the absence of quenching metal ions the dye becomes highly fluorescent. In a broader aspect the phenantroline group is a phenantroline derivative wherein the one, two or three nitrogen skeleton atoms are present in positions different from phenantroline or other derivatives of the phenantrene skeleton of a hydrophobicity allowing penetration into and transporting outwards the cell. In any case the linker L is linked to a carbon corresponding to 9 to 10 of the corresponding phenantrene skeleton. In a particularly preferred embodiment a phenantroline (1,10 isomer) metal chelator is linked to the linker L moiety.

It has been found by the present inventors that in the cells expressing functional ABC multidrug transporters, in particular ABCG2, ABCB1, or ABCC1 transporters, cellular dye fluorescence became strongly reduced.

1,10-Phenanthroline is an inhibitor of metallopeptidases and if the dye comprises such a chelator moiety the loading buffer should be free of metal ion and/or such metal ions should be complexed like by EDTA or a similar chelator.

The assumed mechanism of the invention is explained in more detail on FIG. 8.

As depicted in FIG. 8, the functional presence of any of these three multidrug transporters is capable to reduce PG accumulation, probably by extruding PGD, and potentially also PG. Currently we cannot discriminate between these extrusion effects, but based on earlier studies, most probably the hydrophobic PGD is the main transported substrate of these proteins (see [Homolya L et al. *J Biol Chem.* 1993, Homolya L et al. *Br J Cancer.* 1996; Homolya L et al. *BBA—Biomembr* 2011]). This is the basis of the amplification of the dye extrusion effect in the resulting changes in cellular fluorescence, and the high sensitivity of the assay.

A similar process of esterase cleavage will take place with other compounds of the invention as well and the respective hydroxy forms are obtained as shown on formulae Ma and Mb, respectively. The substituents are those specified in the description of the embodiments of the invention described in detail in the brief description section:

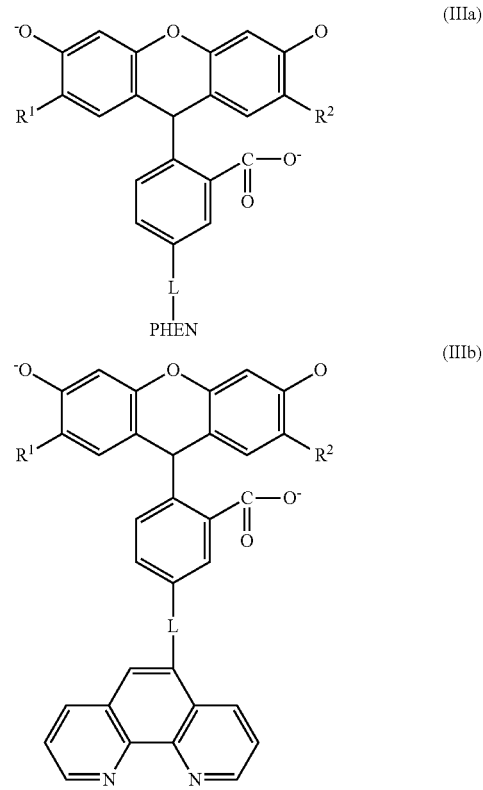

Preparation of such compounds is at hand of a person skilled in the art in analogy with the preparation of Phen-Green compounds.

Moreover, preparation of such compounds is described in U.S. Pat. No. 5,648,270 [Kuhn et al, granted to Molecular Probes Inc, Jul. 15, 1997].

It is of importance that the transport function of key human ABC multidrug transporters can be assessed with a cell permeable fluorescent metal ion indicator.

In an embodiment we examined the potential interactions of three key multidrug transporters, ABCG2 (BCRP), ABCB1 (MDR$^1$, Pgp), and ABCC1 (MRP1) with a compound, originally applied for detecting intracellular metal ion concentrations. PhenGreen diacetate (PGD) is a hydrophobic, cell permeable molecule, which inside the cells is cleaved by cellular esterases into fluorescent PhenGreen (PG), and this hydrophilic product is accumulated inside the cells. Interaction of PG with various metal ions results in the quenching of PG fluorescence, thus allows the quantitative estimation of cellular metal concentrations [Illing A C et al. *J Biol Chem.* 2012]

In case of the ABCB1 and ABCC1 multidrug transporters there are several fluorescence-based transporter assays available to estimate the function of these proteins. The DNA binding dyes, Hoechst 33342, MX and DCV are transported substrates of ABCB1, while these dyes are relatively poorly transported substrates of the ABCC1 protein. Acetoxymethyl esters of several fluorescent indicator dyes are transported by both ABCB1 [Homolya L et al. *Br J Cancer.* 1996], and Calcein-AM, a non-toxic cell viability dye, which is actively extruded by both ABCB1 and ABCC1 [Holló Z et al. *Anticancer Res.* 1998], is widely used for functional studies of these proteins. The transporter-dependent reduced accumulation of free Calcein, generated by cytoplasmic esterases, is a sensitive functional assay for both ABCB1 and ABCC1. In contrast, Calcein AM is not transported by ABCG2, thus this assay system cannot be used in the case of this transporter.

When applying the compounds of the invention PGD treatment and PG accumulation for separation of cells variably expressing specific ABC multidrug transporters, an important point is the potential toxicity of the accumulated PG. As the compounds of the invention are metal ion chelators it was assumed that they may be toxic in assays wherein ABC transporter activity is measured in live cells. Therefore, we have studied if PG accumulation has an effect on cell viability and cell growth.

PGD uptake and PG accumulation cannot be measured in cell culture media, as serum non-specific esterases rapidly cleave PGD to PG, and also, the presence of metal ions significantly change PG fluorescence. Therefore, a direct estimate of PGD cytotoxicity in cell cultures could not be performed, while the relevant, potential cellular effects of PGD and PG were estimated after the experimental period of PG loading.

In highly preferred assay conditions, i.e. in metal ion free medium and low PGD concentrations, ABC transporter function can be particularly sensitively followed e.g. either by flow cytometry or fluorescence microscopy.

In such an application the activity of the three major human ABC drug transporters (ABCB1, ABCC1 and ABCG2) can be quantitatively assessed in the same cellular sample by using a single fluorescence assay for measuring PG accumulation and using specific inhibitors of the individual ABC transporters. This allows a simple and efficient diagnostic application of the assay.

Thus, in a highly preferred assay specific inhibitors of the transporters may be applied to obtain activity values for individual transporters. This is because in the present assay the fluorescence of the fluorescein derivative ester compound used in the invention and/or the corresponding esterase-cleaved hydroxy compound or preferably both, accumulating in the cells is/are and also in a control measurement, having the same parameters but wherein the assay conditions comprise an inhibitor of one or more particular ABC transporters (thereby measurement is also carried out in the population of negative control cells wherein the activity of said particular ABC transporters is inhibited) to obtain a negative control level of the fluorescein derivative compound. Thus, by comparing the level of the fluorescein derivative compound in specimen cells with a negative control level typical of missing ABC transporter activity, a difference value characteristic to the ABC transporters inhibited can be obtained.

In an embodiment only one ABC transporter is inhibited by a specific inhibitor in a single experiment.

In an analogous embodiment in parallel samples or in aliquots obtained from such a sample different ABC transporters are inhibited individually and thereby specific or particular ABC activity values are obtained.

Thereby an ABC transporter activity pattern, i.e. a set of individual ABC transporter activity values can be obtained for a biological sample as illustrated in Example 5 and FIG. 15 for various blood cell population.

In a particular embodiment MAF values are obtained.

This is particularly useful when the method is applied as a diagnostic method to characterize conditions wherein not each ABC transporters, of which the fluorescein derivative ester compound is a substrate, contributes equally to condition or characterizes equally the condition. In other words, increased or decreased level of one or more of the ABC transporters may be indicative of the condition whereas an increase or decrease in the level of other ABC transporters may not be important or should be unchanged or be within a normal range.

Specific inhibitors of ABC transporters and in particular of ABCB1 (MDR1, Pgp), ABCC1 (MRP1) and ABCG2 (BCRP) are well known in the art (see e.g. U.S. Pat. No. 9,097,673).

In a further embodiment it may be of use when two or more (e.g. three) of the ABC transporters to be assessed are inhibited. In such cases a single activity value, in particular a MAF value, is obtained for two or more, e.g. three ABC transporters.

This is particularly useful when in a diagnostic assay the condition to be diagnosed is such that the alteration of the transport activity of the two or more, e.g. three ABC transporters are to be considered, and in the condition sought to be diagnosed the direction of the alteration or modification of the activity is the same. In such cases by using an inhibitor specific to those very transporters the condition can be characterized by a single activity, in particular MAF value for the two or more (e.g. three) ABC transporters.

To give an example, Salvia, Antonella Maria et al. [Hematol Rep. "Expression of some ATP-binding cassette transporters in acute myeloid leukemia" 2017 9(4): 7406] have showed that in Acute Myeloid Leukemia at diagnosis ABCG2 gene is always down-regulated and ABCC1 is always up-regulated compared to healthy donors, while no correlation was observed between ABCB1, ABCC6 and AML. Upon successful drug treatment the level of ABCG2 increases and ABCC1 tends to decrease, bringing their expression values averagely closer to those of healthy subjects, showing that these transporters, above all ABCG2, are closely correlated with AML or rather that their expression may be correlate to the disease and may represent markers of therapeutic response.

This indicates that the present diagnostic assay is also useful to follow or monitor a treatment of the alteration in a condition of a patient as explained below.

Inhibitors inhibiting two or more of ABC transporters and in particular of ABCB1 (MDR1, Pgp), ABCC1 (MRP1) and ABCG2 (BCRP) are well known in the art.

In diagnostic assays the use of inhibitors to obtain a "negative control level" is preferred.

In preferred other embodiments to obtain a negative control level a negative control cell population may be applied, said negative control cell population may be selected from the following types of cells:
cells which express the ABC transporter protein under a pre-determined threshold value,
cells in which the expression of the ABC transporter protein is silenced (or down-regulated).

Lowering the expression of the ABC transporter protein can be achieved by antisense nucleic acid, or e.g. by small interfering RNA or by miRNA once such sequences are known, to give a few examples.

Conditions in which ABC transporters may be assessed, measured of diagnosed according to the invention are known in the art.

It has long been known that multidrug resistance transporters are overexpressed in various tumors or cancers and cancer treatment may involve inhibiting multidrug resistance. Thus, it is an embodiment of the invention to diagnose multidrug resistance in cancer.

Such diagnosis may also involve a patient-specific finding on the multidrug resistance profile of the cancer the patient has. This may also provide information on a possible treatment and also the prognosis of treatment. Thus, the invention also relates to a method for diagnosis and a related treatment which is advised by the diagnosis.

In a preferred embodiment the tumor or cancer is of the blood cells, for example leukemia. For example, Kappelmayer, J et al. [EJIFCC. 2013 23(4): 117-123. "Prediction of Therapy Response and Prognosis in Leukemias by Flow Cytometric MDR Assays"] have reported that therapy response and prognosis is possible in Leukemias by multidrug resistance assays.

Thus, the present assay diagnostic may also be useful to report on a condition which is indicative of a prognosis of a disease, for example a tumor or cancer, e.g. leukemia.

Multidrug resistance ABC transporters have been known to play a role in autoimmune diseases as well. For example, MDR-ABC transporters are expressed in cell types relevant to pathogenesis of rheumatoid arthritis. "Many reports demonstrate the interaction of small molecule drugs with MDR-ABC transporters. Cell-based assays for disease relevant cell types can be easily gated and could reveal specific drug targets and may increase significance and utilisation of data in clinical practice" [Márki-Zay J. Tauberné Jakab K. Szerémy P., Krajcsi P. MDR-ABC transporters: biomarkers in rheumatoid arthritis Clin Exp Rheumatol 2013; 31: 779-787].

Thus, in preferred embodiments conditions include cancers or malignous tumors, preferably cancers of the blood cells or bone marrow cells, e.g. leukaemias.

In further preferred embodiments the conditions include autoimmune diseases.

It follows from the above that diagnosis involves monitoring the condition or alteration of the condition (e.g disease). This means that the method of the invention is to be performed multiple times, preferably by intervals which are recommended in case of the disease.

Also as ABC transporter activity may be used as predictive markers of a condition, the result of the diagnosis may provide an advice on the further treatment. Thus, the invention also relates to a treatment method wherein at first a diagnostic assay method is carried out then the disease is treated in accordance with the result of the diagnosis.

The biological sample depends on the disease to be diagnosed.

For example in case of diseases which are reflected in blood cells the preferred biological sample is blood.

In a preferred embodiment in particular in diagnostic embodiments the assay is carried out in live cells. In this case it may be of importance to measure viability of the cells. This can be carried out by common viability dyes. Such viability dyes are routinely used in fluorimetry and flow cytometry; examples are propidium iodide or 7-aminoactinomycin D. Other dyes the spectrum of which is compatible with that of the present substrates are also applicable.

In diagnostic assays it may also be important to differentiate between cell types or population of cells within the sample.

In case of flow cytemetry measurement, which are preferred according to the invention it this can be done by side-scatter forward scatter (SSC-FSC) gating [Hawley T., Hawley R. (eds) Flow Cytometry Protocols. Methods in Molecular Biology (Methods and Protocols), vol 699. Humana Press] Alternatively specifying the population of cells can be done by antibodies specific to the population of cells. Antibodies may typically be specific to CD markers. This technology is also known to a person skilled in the art; see e.g. [Rühle P F, Fietkau R, Gaipl US and Frey B, Development of a Modular Assay for Detailed Immunophenotyping of Peripheral Human Whole Blood Samples by Multicolor Flow Cytometry, Int. J. Mol. Sci. 2016, 17, 1316] and publications cited therein.

It is documented herein that this assay can be used for the ABCG2, ABCB1 as well as for the ABCC1 drug transporters, providing a new, unique possibility to examine the functional properties of these key human multidrug transporters by using the same reagents and conditions. In addition, low numbers of ABC transporter positive cells can be distinguished and sorted out from mixed cell populations. Moreover, after a short-term PG accumulation the cells do not show a sign of growth change or toxicity. While DNA-reactive fluorescent transporter substrates may cause major genetic alterations, the cytoplasmic PG accumulation does not seem to have such an effect. Therefore, cell sorting and further selective cell culturing can also be supported by this method.

As a summary, the PGD uptake and PG accumulation assay, complemented with the use of selective transporter inhibitors, is a new, highly sensitive tool to examine the functional properties of the key multidrug transporters, for the diagnostic quantitative determination of the ABC transporter activity in clinical samples, and to efficiently select and sort transporter-expressing cells.

EXAMPLES

Materials and Methods
Materials
PhenGreen SK diacetate (PGD) was purchased from Thermo Fischer Scientific (Waltham, MA, US). KO143 was obtained from Tocris Bioscience (Bristol, UK). Benzbromarone and mitoxantrone were purchased from Sigma-Aldrich-Merck (St. Louis, USA). Tariquidar was a kind gift from Dr. S. Bates (NCI, NIH; can be obtained however from Sigma-Aldrich; CAS Number 206873-63-4). The 5D3 antibody was purified from ABCG2-5D3 hybridoma cell line (a kind of gift of Dr. Brian Sorrentino). The 5D3 antibody is also available from Santa Cruz Biotechnology, pn. sc-18841 UniProt no. Q9UNQ0).

QCRL3 with labeled AlexaFluor 488 antibody was obtained from Sony Biotechnology (Surrey, UK). MRK16 antibody was obtained from Kamiya Biomedical Company (Seattle, US). Bxp-21 was purchased from Abcam (Cambridge, UK). C219 antibody was obtained from Enzo Life Sciences (New York, USA). The secondary antibodies (AlexaFluor 488 and 647), Wheat Germ Agglutinin (WGA)-AlexaFluor 647 and TO-PRO™-3 Iodide were purchased from Thermo Fischer Scientific (Waltham, MA, US). Components of phosphate buffered saline were obtained VWR (Radnor, Pennsylvania, USA). All other materials, if unless otherwise were obtained from Sigma-Aldrich-Merck (St. Louis, USA).

Cell Lines

PLB-985 myelomonocytic, HEK-293 human embryonic kidney and A431 skin derived epidermoid carcinoma cell lines, stably expressing the ABCG2 or the ABCB1 protein were generated by using a retroviral transduction system [Elkind N B et al. Iressa. 2005 Özvegy-Laczka C et al. *J Biol Chem.* 2005 Morisaki K et al. *Cancer Chemother Pharmacol.* 2005]. HEK-293 and HL-60 human promyelocytic leukemia cell lines stably expressing ABCC1 were also generated by retroviral transduction [Holló Z et al. *Anticancer Res.* 1998]. Stable expression of the ABC multidrug transporters in these cell lines was regularly examined by specific immunostaining and flow cytometry analysis, using the MRK-16 and C219 (ABCB1), QCRL3 and MRPm6 (ABCC1) and 5D3 and Bxp-21 (ABCG2) antibodies, respectively (see FIGS. 9 to 11).

Blood Sample

Human blood sample was taken by usual procedures. Preferably peripheral blood mononuclear cells are prepared. Handling of blood samples are described e.g. in [Dagur P K and McCoy J P Collection, Storage, and Preparation of Human Blood Cells. Curr Protoc Cytom. 2015; 73: 5.1.1-5.1.16. PMID: 26132177] and references cited therein.

Flow Cytometry

Immunostaining and the transport activity of the ABC transporters were measured by FacsCanto II flow cytometer (BD Bioscience, San Jose, CA) equipped with a blue (488 nm) and red (633 nm) lasers. The PhenGreen (PG) signal was detected in the FITC channel (emission filter: 530/30 nm), mitoxantrone (MX) and TO-PRO-3 signals were detected in the APC channel (emission filter: 660/20 nm).

PhenGreen Accumulation Measurements by Flow Cytometry

In order to follow the time-dependent accumulation of PG, $5 \times 10^5$ cells were washed twice with 1 mL DPBS (1 g/L D-glucose with phosphate buffered saline), then pre-incubated in the uptake buffer (1 mM EDTA in DPBS) for 10 minutes at 37° C. Thereafter the cells were incubated in the uptake buffer with various concentrations of PhenGreen SK diacetate (PGD), with or without transporter inhibitor, at 37° C., for 1-60 minutes. Dye uptake was stopped by the addition of 150 μl ice-cold EDTA-DPBS, the cells were kept on ice until the measurements (see FIG. 12.). For assessing the PGD concentration dependence of PG accumulation, $5 \times 10^5$ PLB-985 or A431 cells, expressing the ABCB1 or ABCG2 transporters, or HL-60 and HEK-293 cells, expressing ABCC1, were washed twice with 1 mL DPBS, then pre-incubated in EDTA-DPBS medium for 10 minutes at room temperature. The cells were incubated in EDTA-DPBS with 0.1-5 μM of PGD at 37° C. for 30 minutes. Dye uptake was stopped by the addition of 150 μl ice-cold EDTA-DPBS. The cells were kept on ice until the measurement.

For assessing transporter inhibition, the ABCG2 transporter function was inhibited by 2.5 μM KO143 (KO), ABCB1 by 0.25 μM tariquidar (TQ), and ABCC1 by 50 μM benzbromarone (BB). The cells ($5 \times 10^5$) were incubated with 0.5 μM PGD or 1 μM (Mx) with or without inhibitors, for 30 (PGD) or 60 (Mx) minutes at 37° C. The reaction was stopped by the addition of ice-cold EDTA-DPBS and fluorescence was measured as described above.

In order to the potential effects of metal ions in the cells or in the media, we have used EDTA both in the washing and incubation media. Without the use of this metal chelator we obtained variable results for the transporter activity, while the use of EDTA in all media allowed reproducible studies, and made it unlikely that cellular metal concentrations would affect the probe fluorescence or its transport properties.

The efflux of PhenGreen was measured by FACS Aria III Cell sorter (BD Bioscience, San Jose, CA, with 488 nm blue laser excitation and 530/30 nm emission). The control, and ABCG2, ABCB1 or ABCC1 transporter expressing cells were treated with specific transporter inhibitors (ABCG2 by 2.5 μM KO, ABCB1 by 0.25 μM TQ, and ABCC1 by 50 μM BB). The cells were incubated with 1 μM PGD in EDTA-DPBS for 30 minutes at 37° C., then washed three times and the efflux measured continuously for 40 minutes at 37° C.

Flow Cytometry Data Analysis

All experiments were performed at least three times. Data analysis was performed using FACSDiva v6.1.3 Software (BD Bioscience, San Jose, CA), flow cytometry figures were prepared with the Attune Acoustic Focusing Cytometer v1.25 Software (Applied Biosystems, Life Technologies, Carlsbad, CA, USA). Results were expressed as median±standard deviation. The MDR activity factor % (MAF %—see refs [Homolya L et al. *Br J Cancer.* 1996; Holló Z et al. *Anticancer Res.* 1998; 18: 2981-7., Sarkadi et al. U.S. Pat. No. 5,872,014 1999]) was calculated as follows: MAF %=$(((MFI_{inh}-MFI_0)/MFI_{inh}) \times 100)$, wherein $MFI_{inh}$ and $MFI_0$ are the median fluorescence intensity (MFI) with (inh) or without (0) inhibitor. The $EC_{50}$ analysis was carried out using the Origin 8.6. software.

Cell Viability Assay

Control and ABCG2 expressing PLB-985 cells ($1 \times 10^6$) were pre-incubated in the uptake buffer for 10 minutes at 37° C., then incubated with or without 0.5 μM PGD for 30 minutes at 37° C. The PGD-treated cells were sorted based on PG fluorescence by FACS Aria III Cell sorter (BD Bioscience, San Jose, CA, with 488 nm blue laser excitation and 530/30 nm emission). The sorted cells were suspended in 3 mL RMPI media in 6 well plates and live cell number was measured each day, dead cells were excluded by TO-PRO™-3 Iodide.

In order to estimate the $EC_{50}$ values, HEK or A431 cells were treated with 0.5 μM PGD for 30 min at 37° C. in the EDTA-DPBS buffer, then washed and cultured in 2 mL DMEM media in 12 well plates for 72 hours. Live cell number was determined by FACSCantoII flow cytometry, dead cells were excluded by TO-PRO™-3 Iodide.

Confocal Images

For confocal microscopy the cells ($5 \times 10^5$) were washed twice with 1 mL DPBS, then pre-incubated with 1 μg/mL Alexa Fluor-647 conjugated wheat-germ agglutinin (WGA- A647) in uptake buffer for 5 minutes at room temperature. Thereafter the cells were incubated with 0.5 µM PGD with or without transporter inhibitors for 30 minutes at 37° C. PGD uptake was stopped by washing the cells with 1 mL DPBS. The images were acquired by a Zeiss LSCM 710 microscope using a 63×NA=1.4 Plan Apo objective. Images were captured and analyzed by Zen2 (Blue edition) Software.

Example 1—Cell Lines and Assay Conditions

Figure 9:
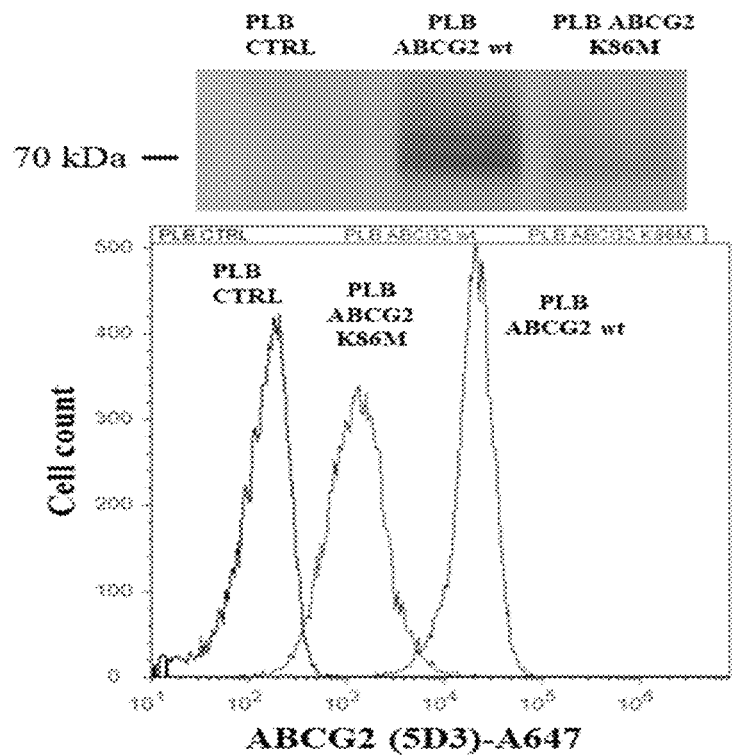
Figure 9:
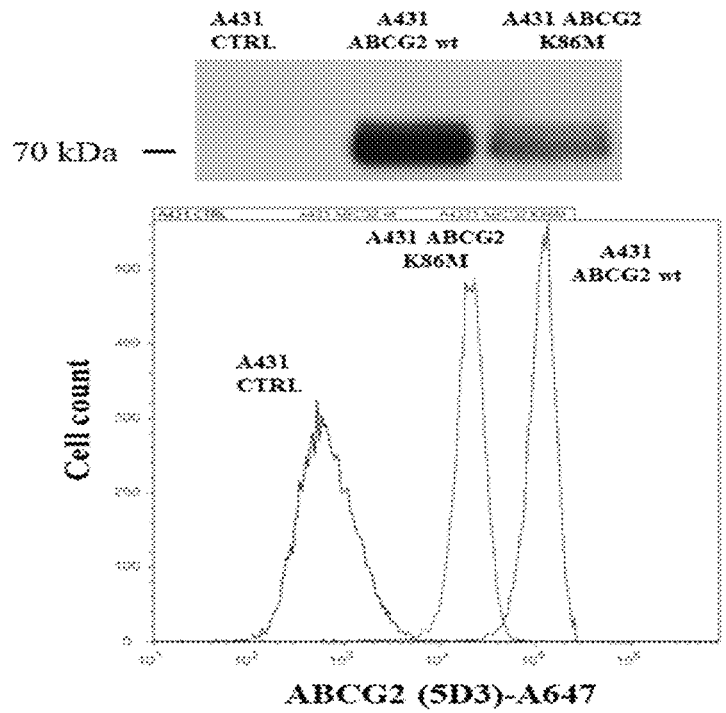
Figure 10:
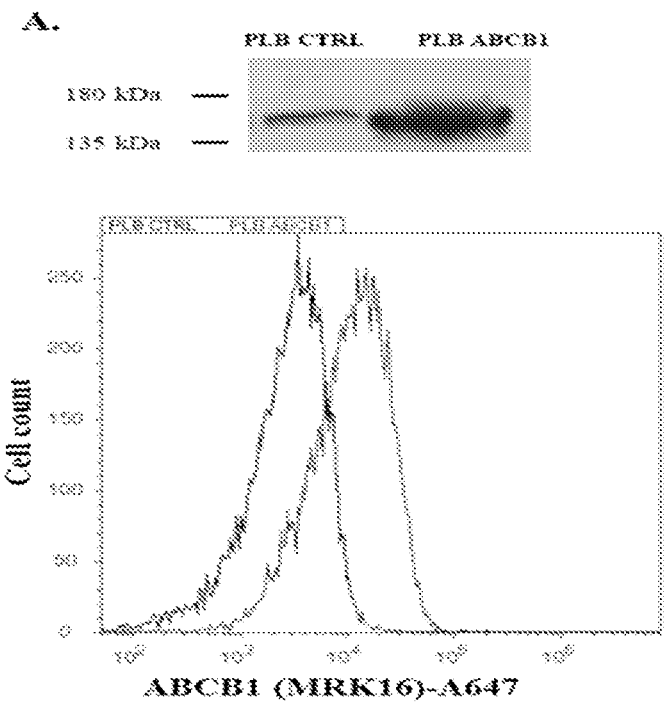
Figure 10:
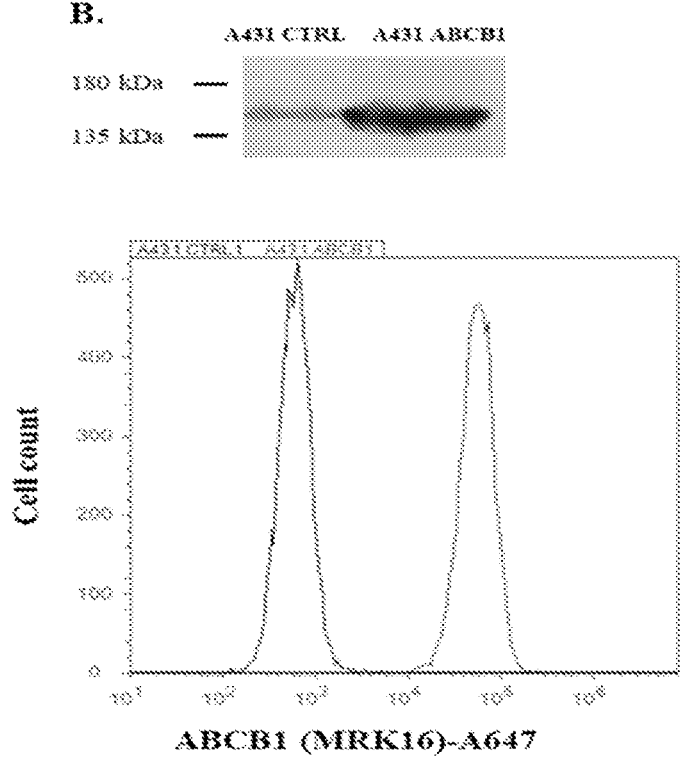
Figure 11:
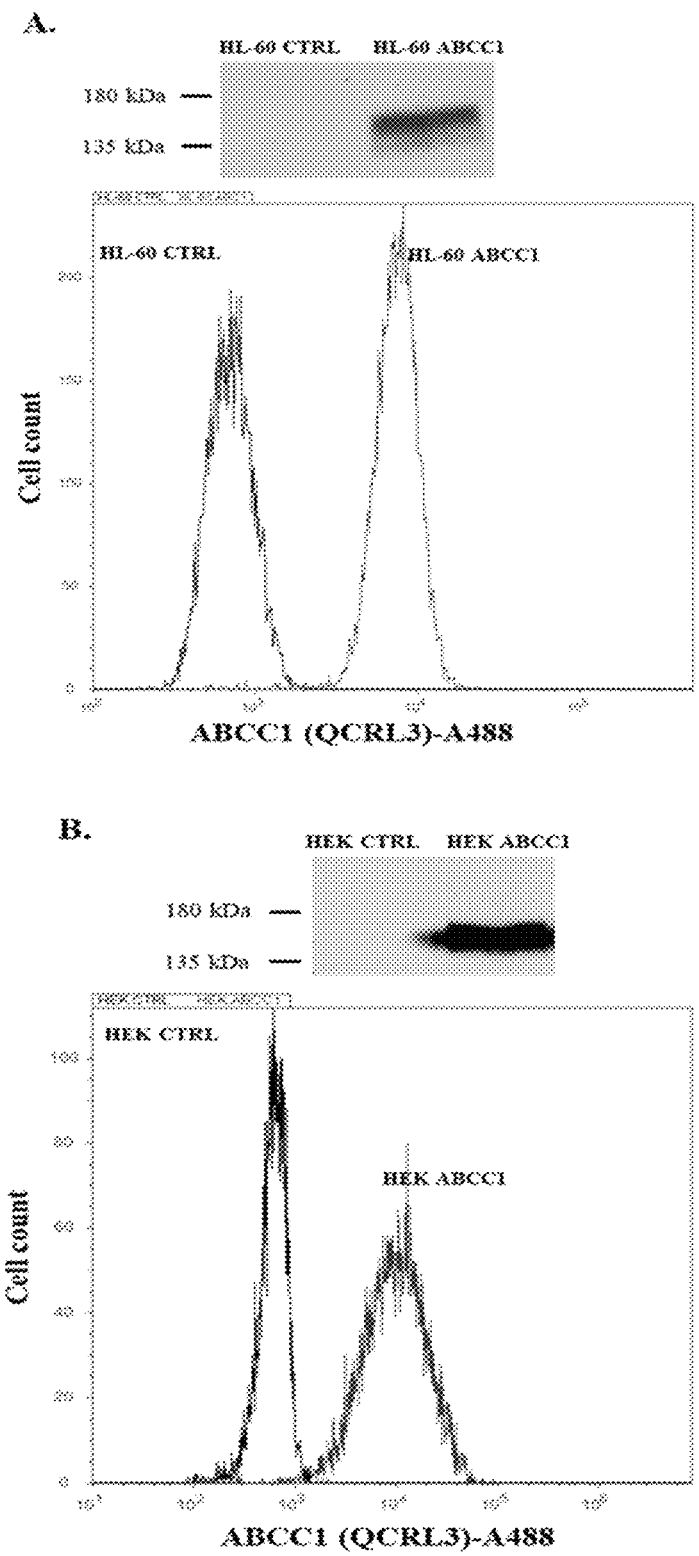

In order to investigate the interactions of the ABC transporters with PGD, we used various cell lines expressing ABC transporters. As described in the Materials and methods section, and documented in detail in the FIGS. 9-11, the stable and selective overexpression of the respective transporters was assured by continuous examination of the transporter levels by immunostaining in flow cytometry and Western blotting. The cell lines applied in this study included the PLB/HL-60 lymphoblastoid cells, selectively overexpressing ABCG2, ABCB1 or ABCC1, the A431 cells overexpressing ABCG2 or ABCB1, and the HEK cells, overexpressing ABCC1. In each case the respective control cells, with unmeasurably low expression levels of these transporters, were also applied (FIGS. 9-11).

In order to select appropriate conditions for studying the effects of ABC transporters on cellular PG accumulation, we examined the rate of PGD uptake and PG accumulation in the applied cell lines, at various PGD concentrations (between 0.5-2.5 µM) in the media. In these studies, we used metal-free media (see Methods) in order to exclude quenching of the PG fluorescence. Based on several trial conditions, as an optimal, non-toxic media for the cell based assays we used the glucose-containing DPBS, supplemented with 1 mM EDTA.

As shown in a time-course experiment documented in FIG. 12, in the PLB cells, when 0.5 to 2.5 µM PGD was applied in the media, the increase in cellular PG fluorescence at 37° C. saturated in less than 30 minutes. Also, under these conditions the effects of the ABC transporters (shown for ABCG2 in Supplementary FIG. 12), could be well assessed. Similar time-dependent PG accumulation was found in the other cell lines applied (not shown).

Example 2—Effects of ABCG2 on Fluorescent PG Accumulation

Figure 1:
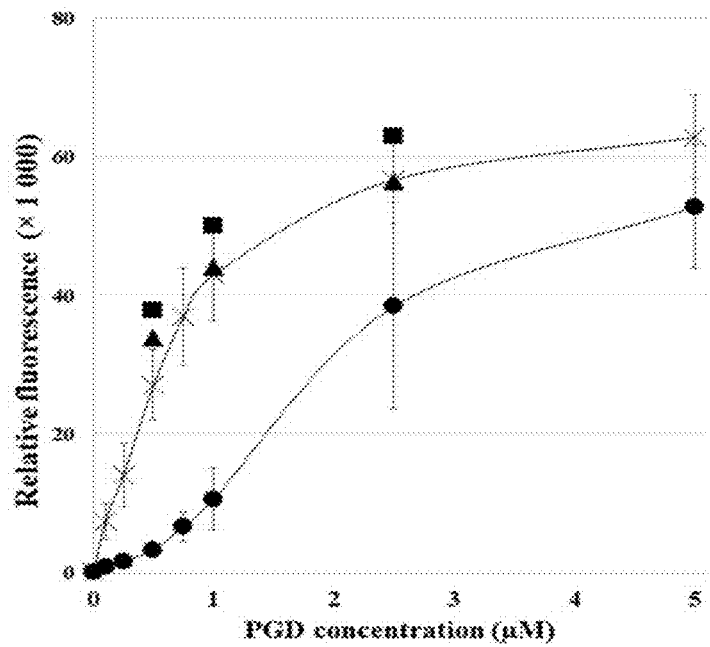
FIG. 1. Fluorescent PG accumulation in human cells, effect of ABCG2 expression—flow cytometry studies. Panel A. PGD-concentration dependent PG accumulation in control PLB cells (x) and in PLB-ABCG2 cells (●). The black squares (■: ABCG2) and triangles (▲: CTRL) demonstrate PG accumulation in the presence of 2.5 μM KO143, a specific ABCG2 inhibitor. Panel B. PGD-concentration dependent PG accumulation in control A431 (x) and A431-ABCG2 (●) cells, measured in EDTA-DPBS medium for 30 minutes at 37° C. The black squares (■: ABCG2) and triangles (▲: CTRL) demonstrate PG accumulation in the presence of 2.5 μM KO143 at 0.5 μM PGD.±SD values are indicated.
Figure 1:
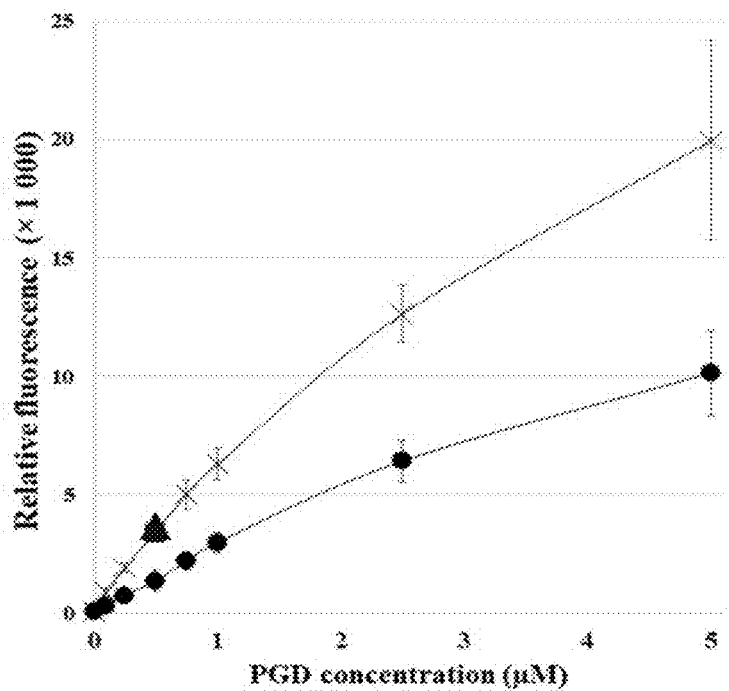

In the first set of experiments we analyzed in detail the effects of the cellular ABCG2 multidrug transporter expression on PG accumulation. FIG. 1A shows the PGD-concentration dependence of PG accumulation in control PLB cells and in PLB-ABCG2 cells, respectively, as measured by flow cytometry. [Panel A. PGD-concentration dependent PG accumulation in control PLB cells (x) and in PLB-ABCG2 cells (●). The black squares (■: ABCG2) and triangles (▲: CTRL) demonstrate PG accumulation in the presence of 2.5 µM KO143, a specific ABCG2 inhibitor.] FIG. 1B shows in similar experiments the PGD-concentration dependence of PG accumulation in control A431 and in A431-ABCG2 cells. [Panel B. PGD-concentration dependent PG accumulation in control A431 (x) and A431-ABCG2 (●) cells, measured in EDTA-DPBS medium for 30 minutes at 37° C. The black squares (■: ABCG2) and triangles (▲: CTRL) demonstrate PG accumulation in the presence of 2.5 µM KO143 at 0.5 µM PGD.±SD values are indicated.] As documented, in the PLB cells at low (below 1 µM) PGD concentrations the presence of the ABCG2 protein in the cell membrane causes a major difference in the amount of the accumulated PG fluorescence, and this difference becomes somewhat smaller at higher PGD concentrations. In the case of the A431 cells, at increasing PGD concentrations the difference in cellular fluorescence caused by the ABCG2 protein still increases, while the ratio of the fluorescence values in the absence and presence of ABCG2, respectively, does not increase. Therefore, in our further experiments we used a PGD concentration of 0.5 µM, which was found sufficient to provide optimum functional assay conditions.

In the following experiments we have studied the effects of ABCG2 variants and mutations of the cellular PG accumulation, and compared these effects with those on cellular mitoxantrone (MX) accumulation. MX is a well-established fluorescent transported substrate of the ABCG2 protein, and this drug is widely used to assess ABCG2 function. However, MX is a strongly cytotoxic agent and cannot be used for separation or further culturing of transporter expressing cells.

Figure 2:
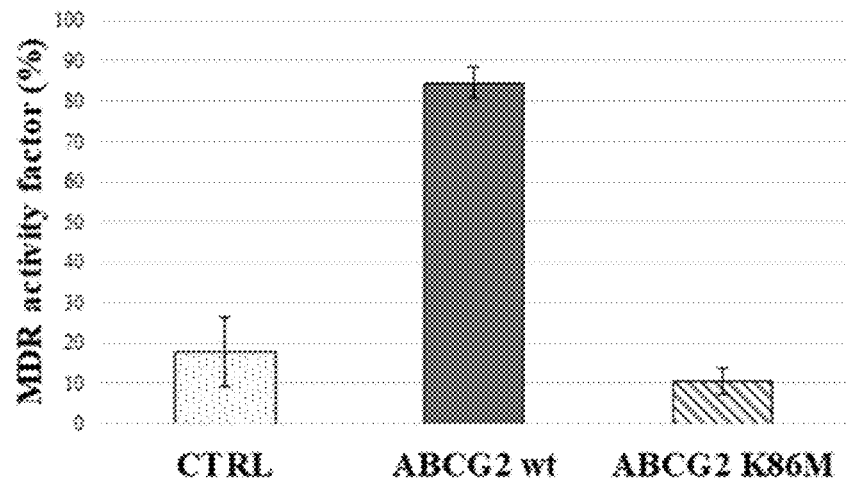
FIG. 2. MDR activity factors based on PG and mitoxantrone (MX) accumulation in human PLB and A431 cells. Effects of the ABCG2 variants on dye extrusion capacity—flow cytometry studies. Panels A. and B.: MDR activity factor (see Methods) calculated by PG accumulation in PLB cells (Panel A) and A431 cells (Panel B), expressing ABCG2 variants. Panels C. and D.: MDR activity factor calculated by MX accumulation in PLB cells (Panel C) and A431 cells (Panel D), expressing ABCG2 variants. +/−SD values are indicated.
Figure 2:
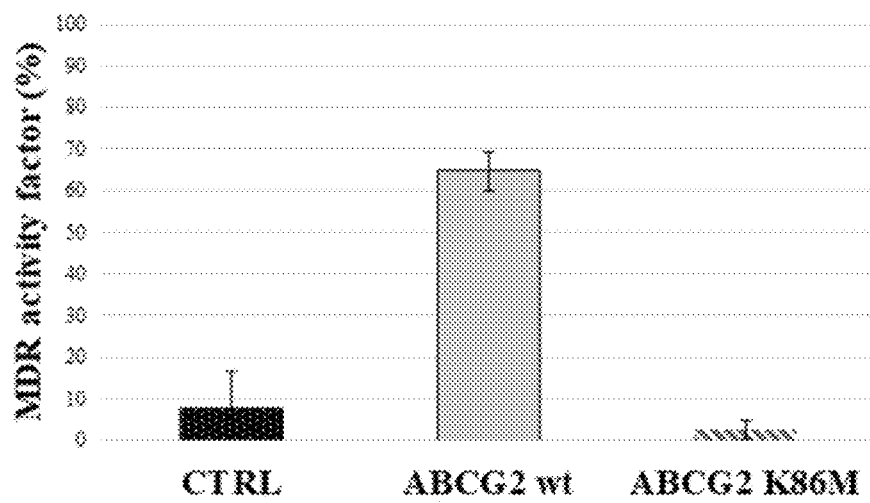
Figure 2:
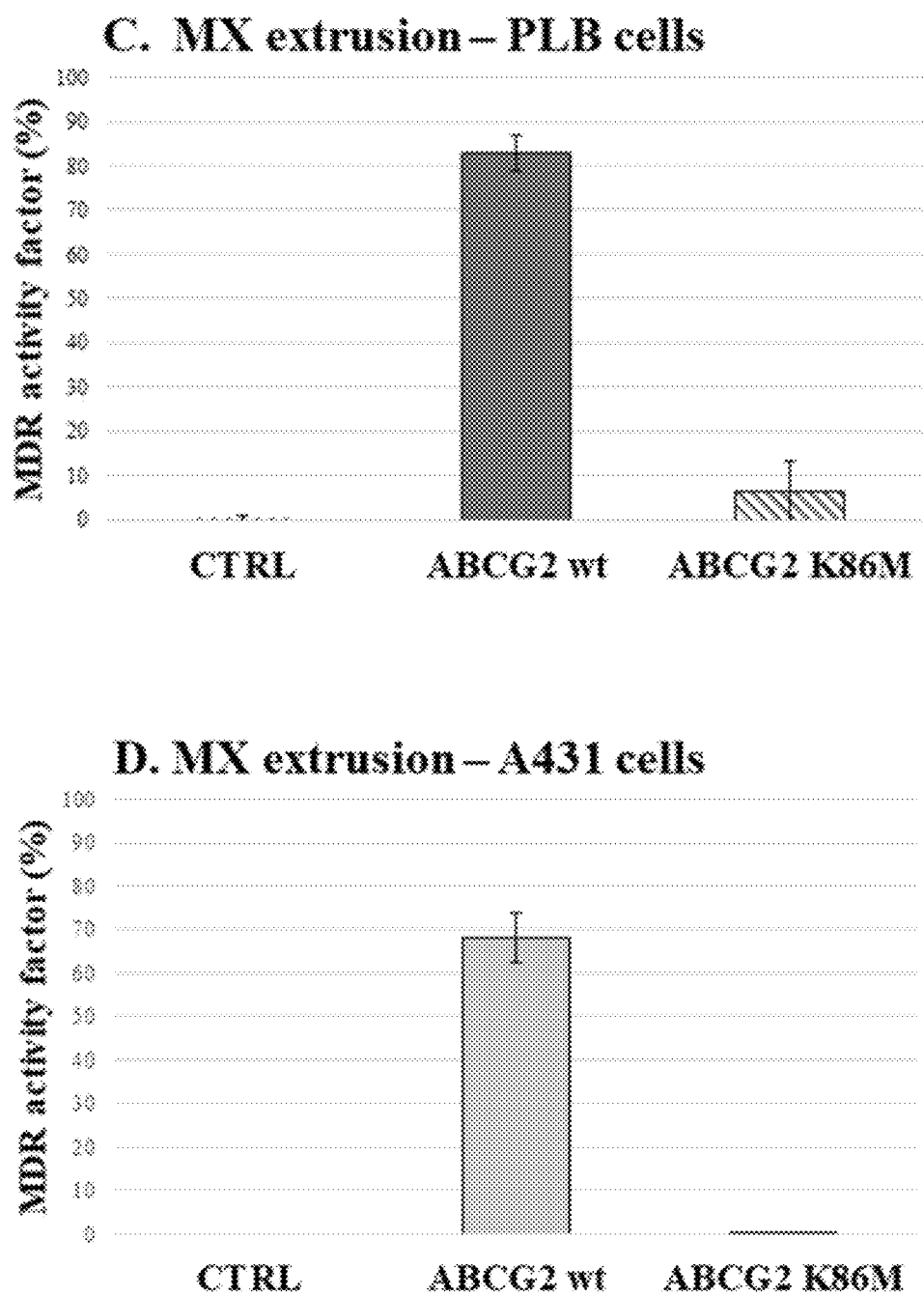

In the experiments shown in FIG. 2, we present the multidrug resistance (MDR) activity factors, i.e. MAF in short (see refs [Homolya L et al. *Br J Cancer*. 1996, Holló Zs et al., *Anticancer Res*. 1998, Hollo, Zs et al. EP 0784699 B1, 1999] calculated from the differences in the fluorescent cellular PG accumulation, found in the absence or the presence of a specific inhibitor of ABCG2, Ko143. As shown in Panel A, control PLB cells have a very low level of MDR activity, while PLB cells expressing the wild-type (wt) ABCG2 protein show a high activity level. In order to demonstrate the role of ABCG2 transporter activity in this process, we also examined the effect of the non-functional catalytic mutant ABCG2-K86M on PG accumulation. This mutant variant, also with somewhat lower membrane expression (see FIGS. 9A and B) had no effect on PG accumulation, thus produced a low MDR activity factor. Panel B documents similar PG accumulation studies in control and ABCG2 expressing A431 cells, respectively, with essentially the same findings in this cell line.

In parallel experiments we have also calculated the MDR activity factor (MAF) based on MX extrusion, in the control and ABCG2 expressing PLB (Panel C) and A431 cells (Panel D), respectively. As shown in Panels C and D in FIG. 2, MX extrusion measurements gave essentially similar results as obtained by using PG accumulation.

In order to examine the wider applicability of the PGD-based assay for functional ABCG2 transporter studies, we examined PG accumulation in control PLB cells and in PLB cells expressing ABCG2, by using fluorescence (confocal) microscopy. PG fluorescence (green) was examined after 30 minutes of the addition of 0.5 µM PGD to the medium, either in the absence or presence of the ABCG2 inhibitor KO143 (2.5 µM).

In these experiments, in order to label the plasma membrane compartment of the cells, we also included the staining of live PLB cells with a fluorescent anti-WGA antibody.

Figure 3:
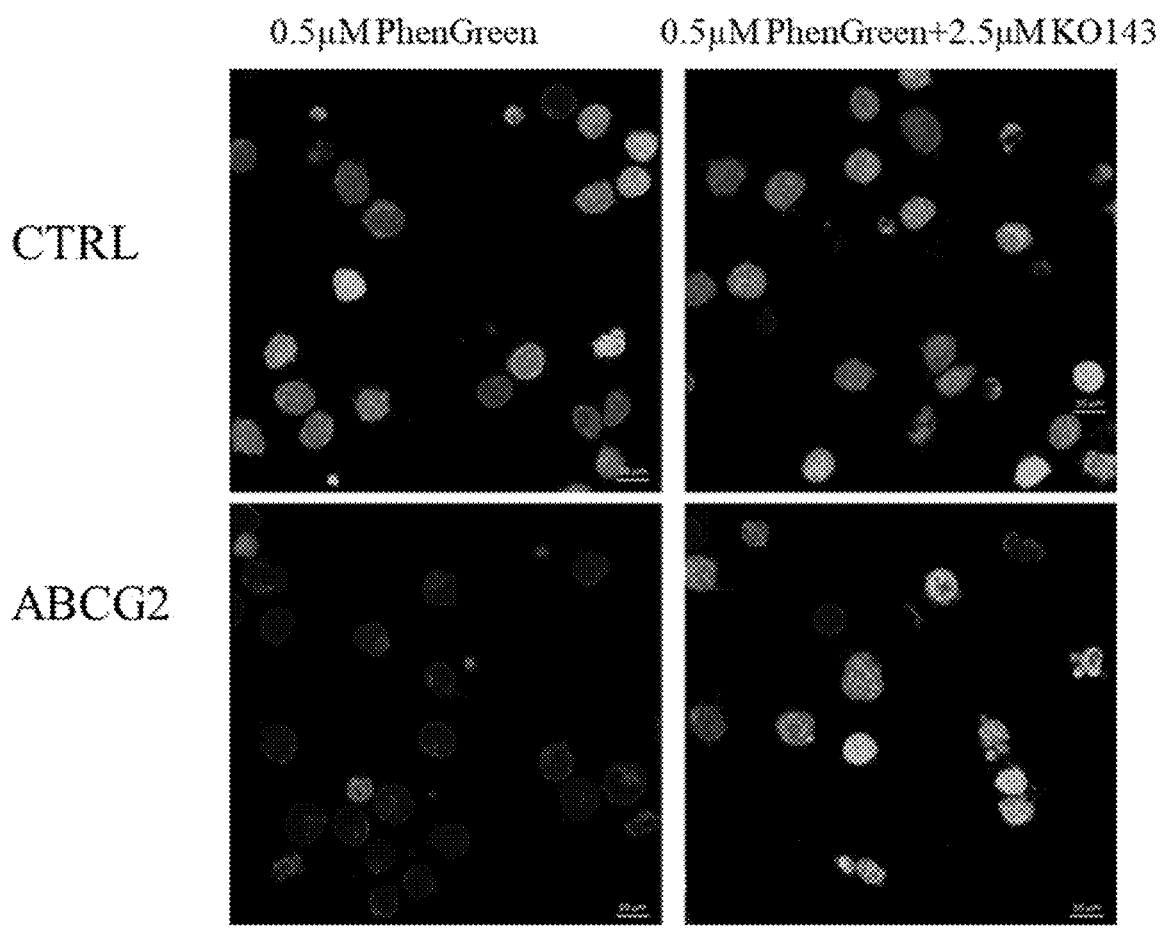
FIG. 3. Fluorescent PG accumulation in human PLB cells, examined by confocal microscopy. Effects of ABCG2 protein expression and inhibition of its function by Ko143. PG fluorescence (green) was examined after 30 minutes of the addition of 0.5 μM PGD to the medium, either in the absence or presence of the ABCG2 inhibitor KO143 (2.5 μM) in cells pre-labeled with fluorescent anti-WGA (red).

As shown in the representative confocal microscopy images in FIG. 3, control PLB cells showed an intensive green signal (shown in many cells as filled in light grey, is some of the in a darker tone) due to the cytoplasmic accumulation of PG, while the PLB-ABCG2 cells practically did not accumulate PG (dark cell with fluorescence typically in their membranes only). Upon the addition of the specific ABCG2 inhibitor, Ko143, cellular fluorescence in the ABCG2 expressing cells was greatly increased. The cells pre-labeled with fluorescent anti-WGA show fluorescence at the plasma membranes (shown typically as a medium grey, originally red, circle on the figure).

Figure 4:
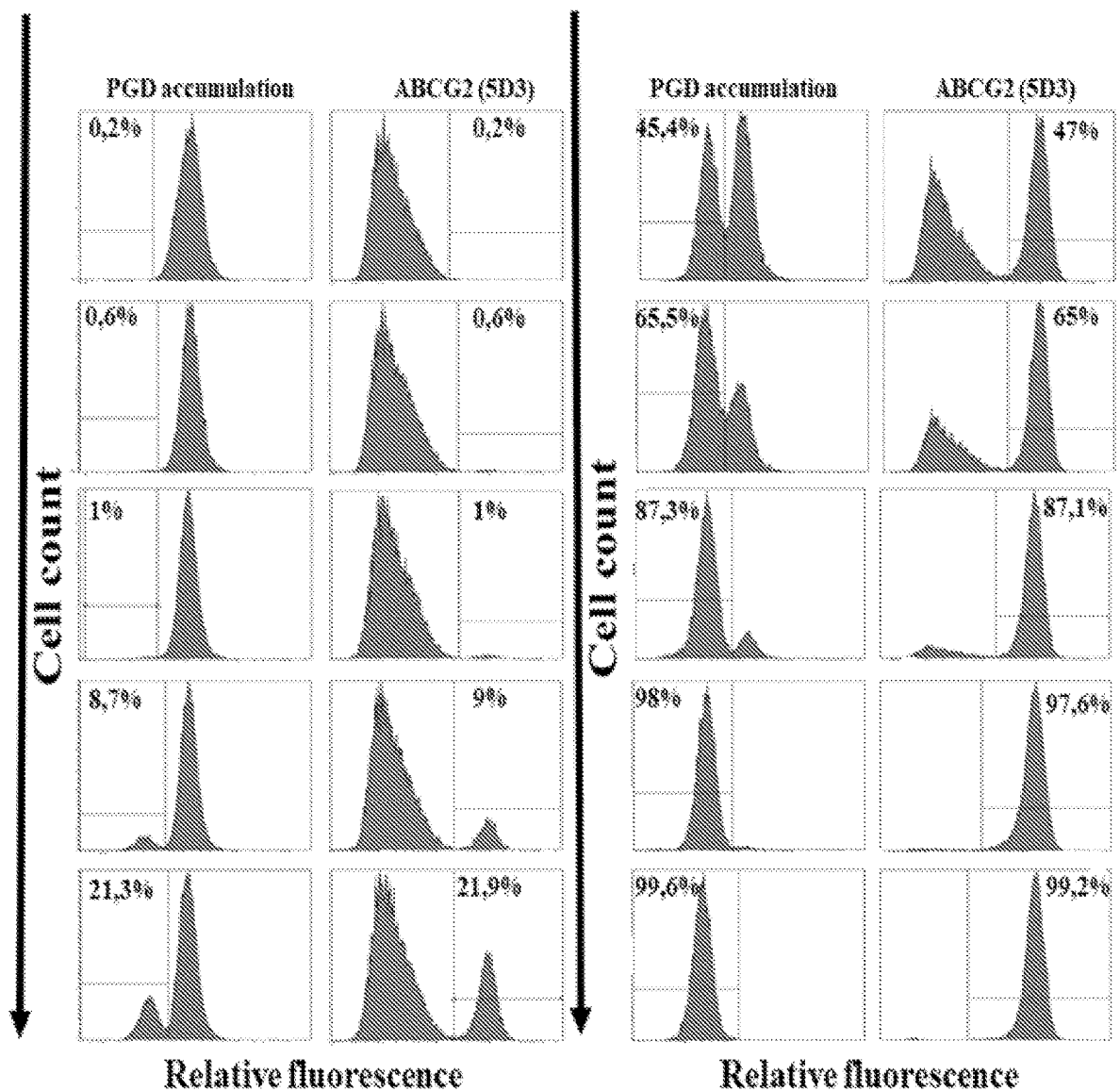
FIG. 4. Flow cytometry detection of PG accumulation in human PLB cells—recognition and separation of control PLB cells and PLB cells expressing the ABCG2 transporter. Control PLB cells and PLB cells expressing wild-type ABCG2 were mixed in various ratios (0.2-99.8%). PG accumulation was measured after the addition of 0.25 μM PGD Immunofluorescent detection of the ABCG2 protein on the cell surface of the same cells was measured by the ABCG2-specific 5D3 monoclonal antibody binding. The numbers on the graphs indicate the % values of the separated cells, measured based on the relative fluorescence values.

In the following experiments we examined the potential use of the PG accumulation assay for the selection of cells expressing the ABCG2 protein. In case of tissue-derived or tumor stem cells the expression of the ABCG2 protein causes the appearance of a Side Population (SP), originally observed based on the Hoechst 33342 dye extrusion, due to the function of the ABCG2 protein (refs. [Telford W G, et al. *Stem Cells.* 2007; Boesch M, et al. *Cytom Part A.* 2012; Sheng Z, et al. *Nat Med.* 2001]). Control PLB cells and PLB cells expressing wild-type ABCG2 were mixed in various ratios (0.2-99.8%). PG accumulation was measured after the addition of 0.25 μM PGD Immunofluorescent detection of the ABCG2 protein on the cell surface of the same cells was measured by the ABCG2-specific 5D3 monoclonal antibody binding. The numbers on the graphs indicate the % values of the separated cells, measured based on the relative fluorescence values (see Materials and methods). The results are documented in FIG. 4. Based on low PG accumulation and its increase by the ABCG2 inhibitor KO143, even cell populations representing less than 1% of the total cell mixture, can be visualized and separated by using flow cytometry. This functional assay is similarly highly sensitive as the cell surface labeling of the ABCG2 protein by a specific monoclonal antibody, 5D3 (see FIG. 4).

Example 3—Effects of ABCB1 and ABCC1 on Fluorescent PG Accumulation

As shown above, the PG accumulation assay provides a sensitive assay for ABCG2 activity, therefore in the following experiments we examined if PG accumulation can also be applied to study the function of ABCB1 and/or ABCC1.

Figure 5:
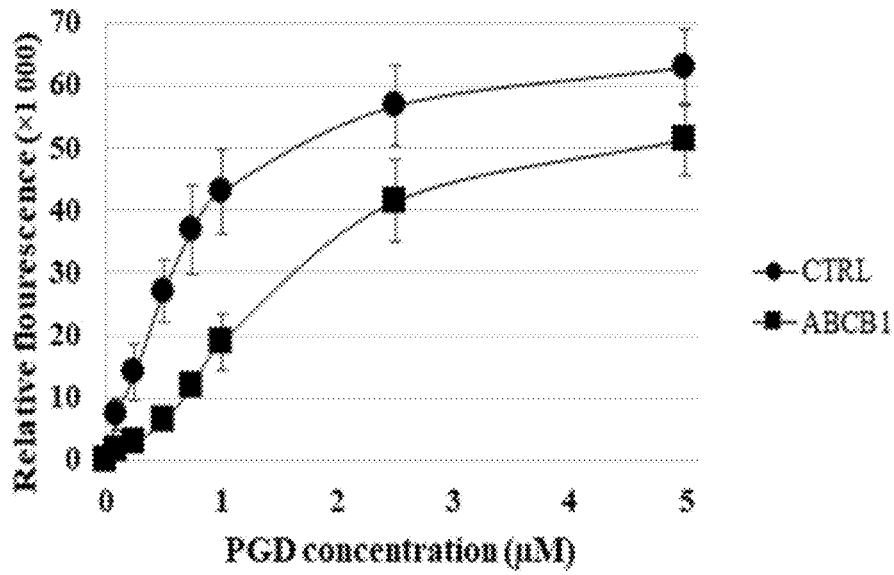
FIG. 5. Fluorescent PG accumulation in human cells, effects of ABCB1 and ABCC1 expression—flow cytometry studies.
Figure 5:
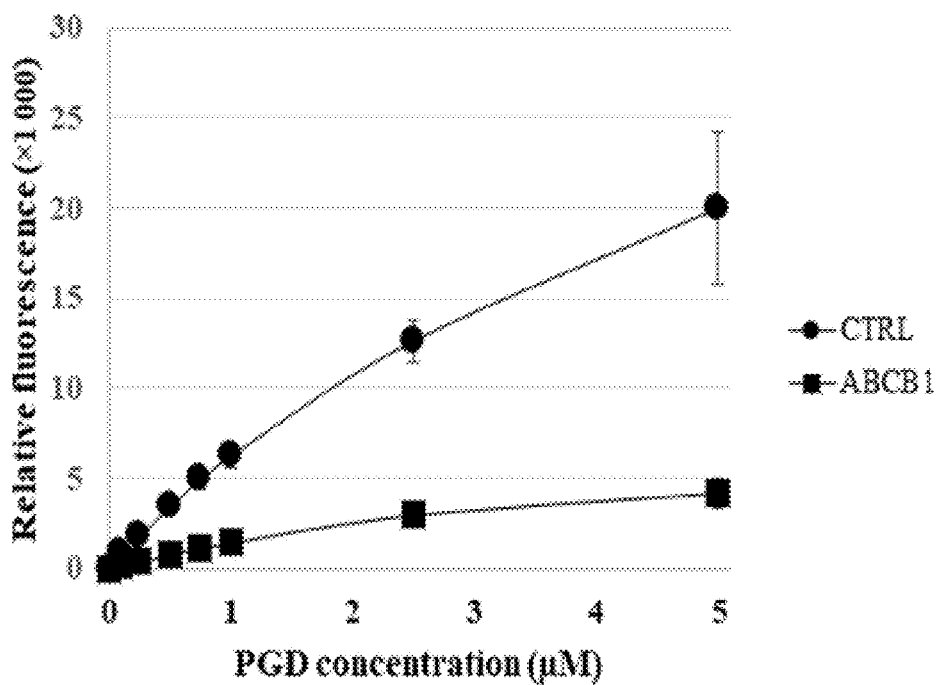
Figure 5:
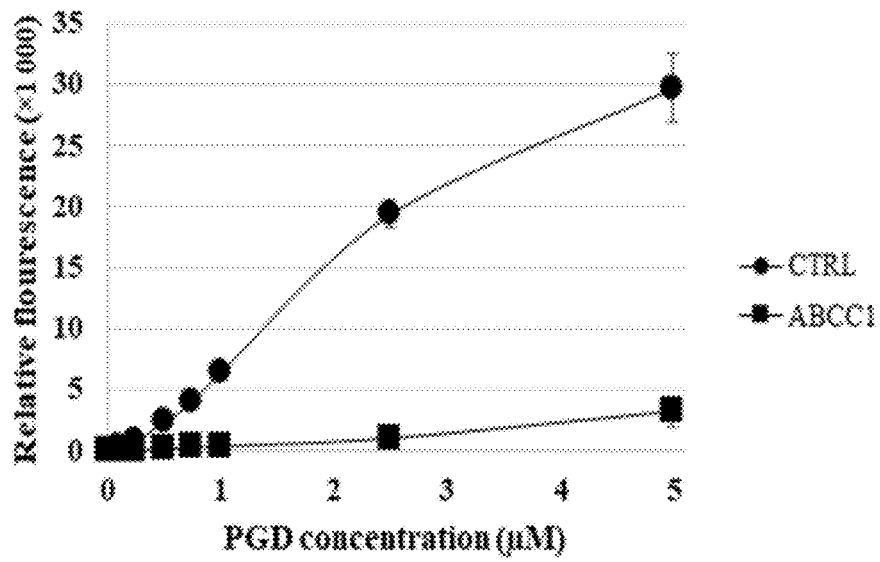
Figure 5:
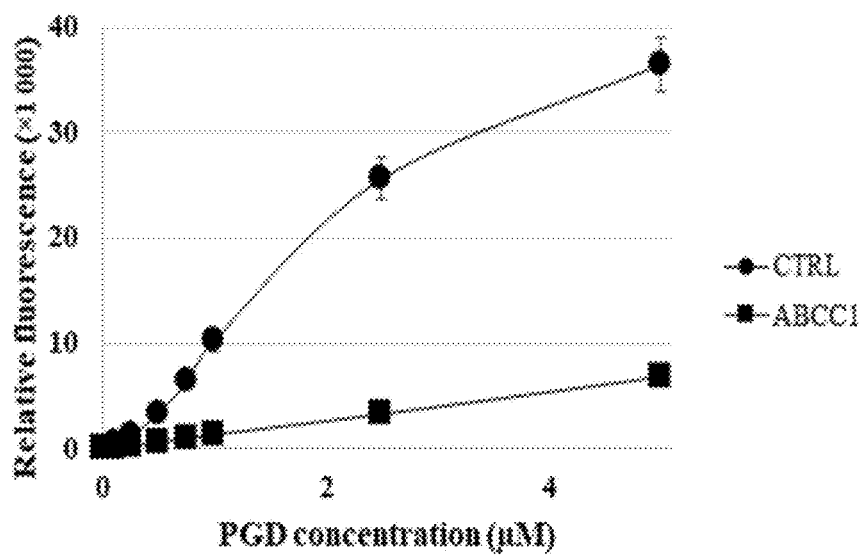
Figure 5:
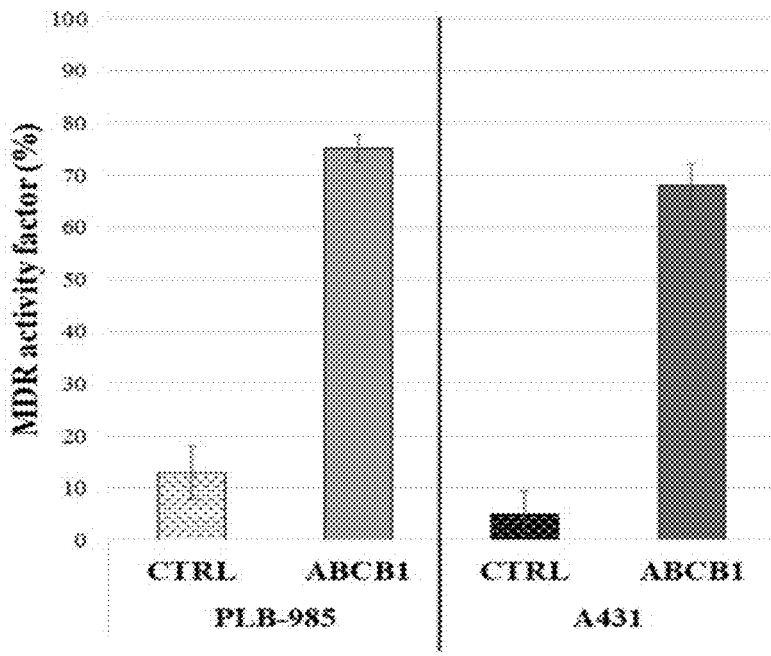
Figure 5:
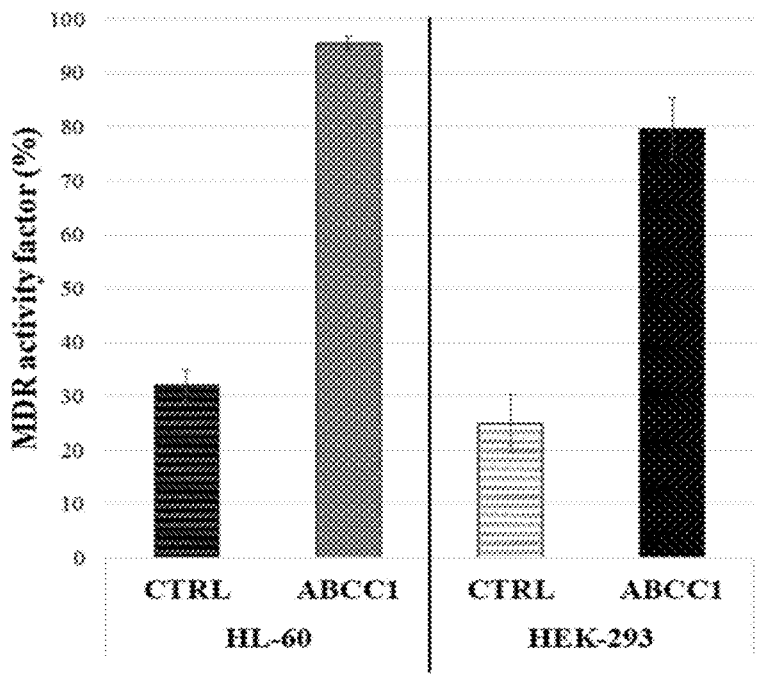

As shown in FIG. 5, in various human cell lines, expressing either ABCB1 or ABCC1, PG accumulation is significantly decreased. In a relatively wide concentration range, that is between 0.1-5 μM, ABCB1 or ABCC1 expressing cells accumulate significantly lower levels of PG than their control parental cells (Panels A and B: ABCB1 expressing PLB and A431 cells, respectively, with their respective controls; Panels D and C: ABCC1 expressing HL-60 and HEK cells, respectively, with their respective controls.). The cells were incubated in the presence of variable PGD concentrations (0.1-5 μM) in EDTA-DPBS medium for 30 minutes at 37° C., and fluorescent PG accumulation in the cells was measured by flow cytometry.

As shown in FIG. 5 Panel E, the MDR activity factor can be calculated both by comparing the parental and transporter expressing cells, or by using specific inhibitors of ABCB1 (tariquidar) or ABCC1 (benzbromarone).

Figure 14:
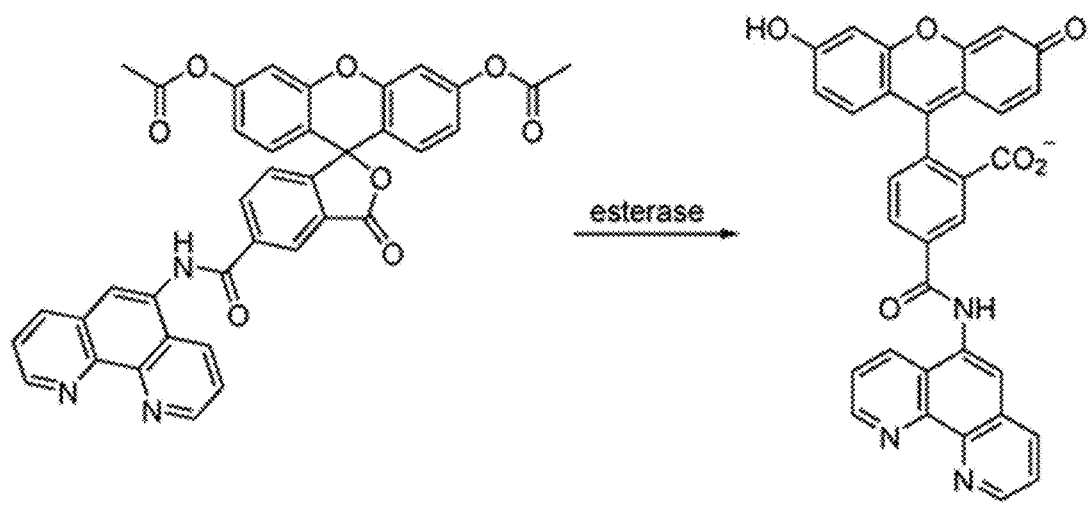
Figure 15A:
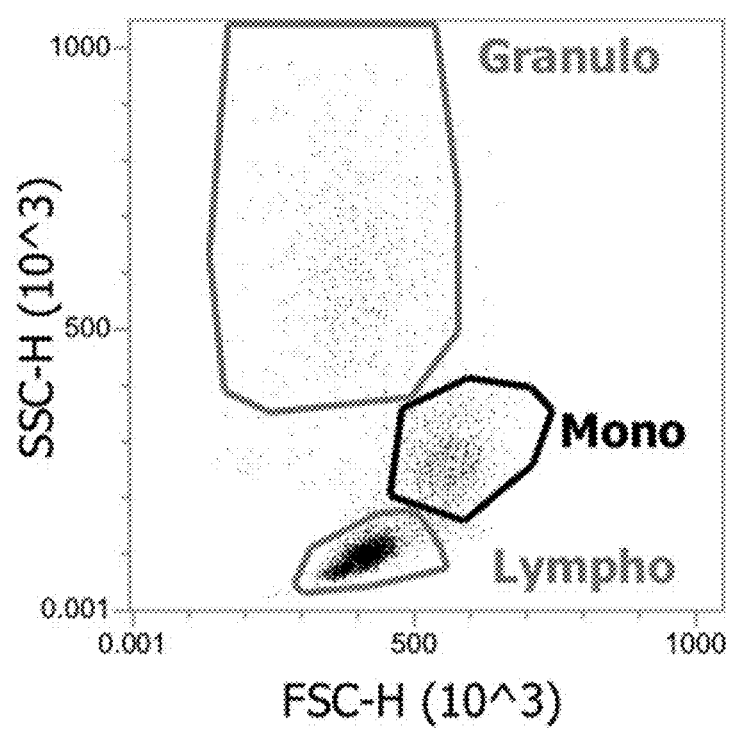
Figures 1, 15B:
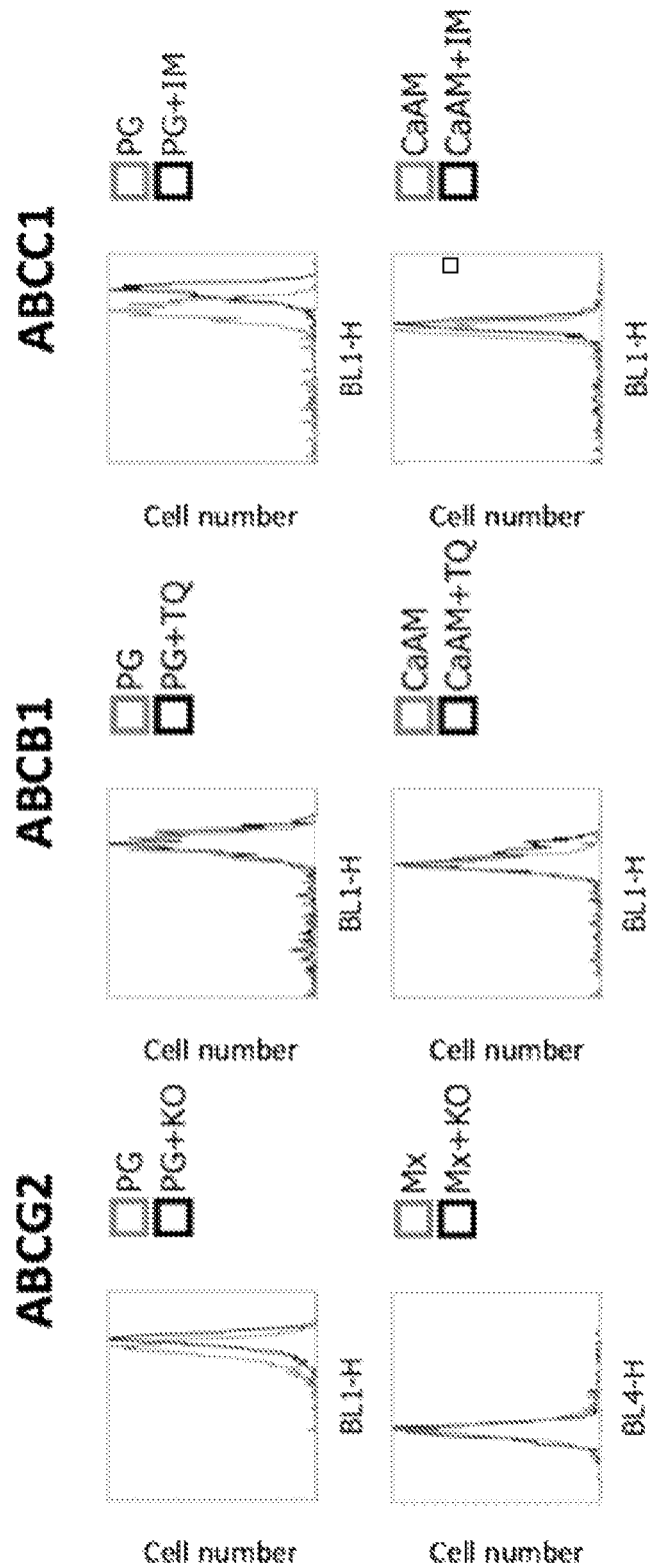
Figures 2, 15B:
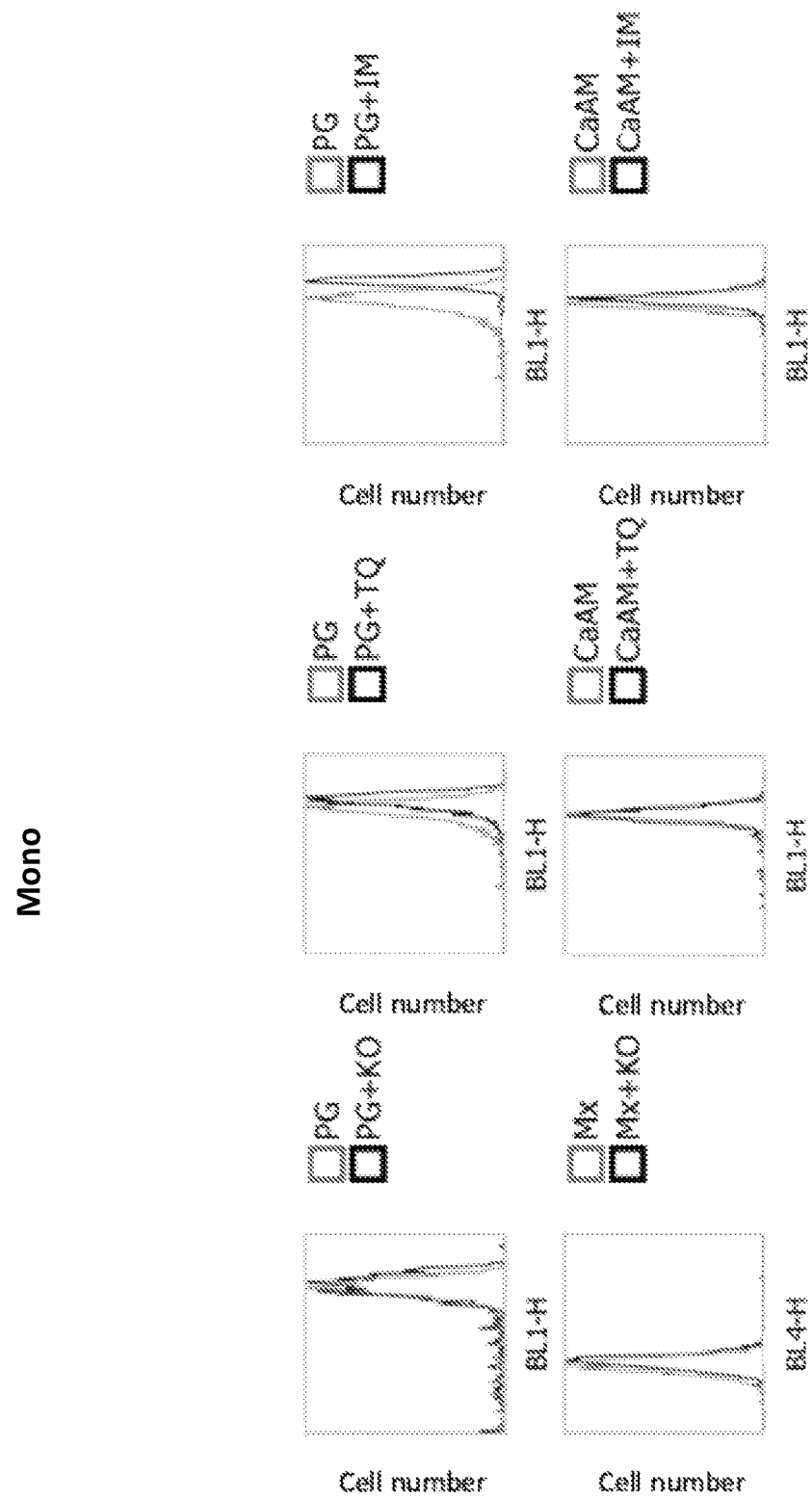
Figures 3, 15B:
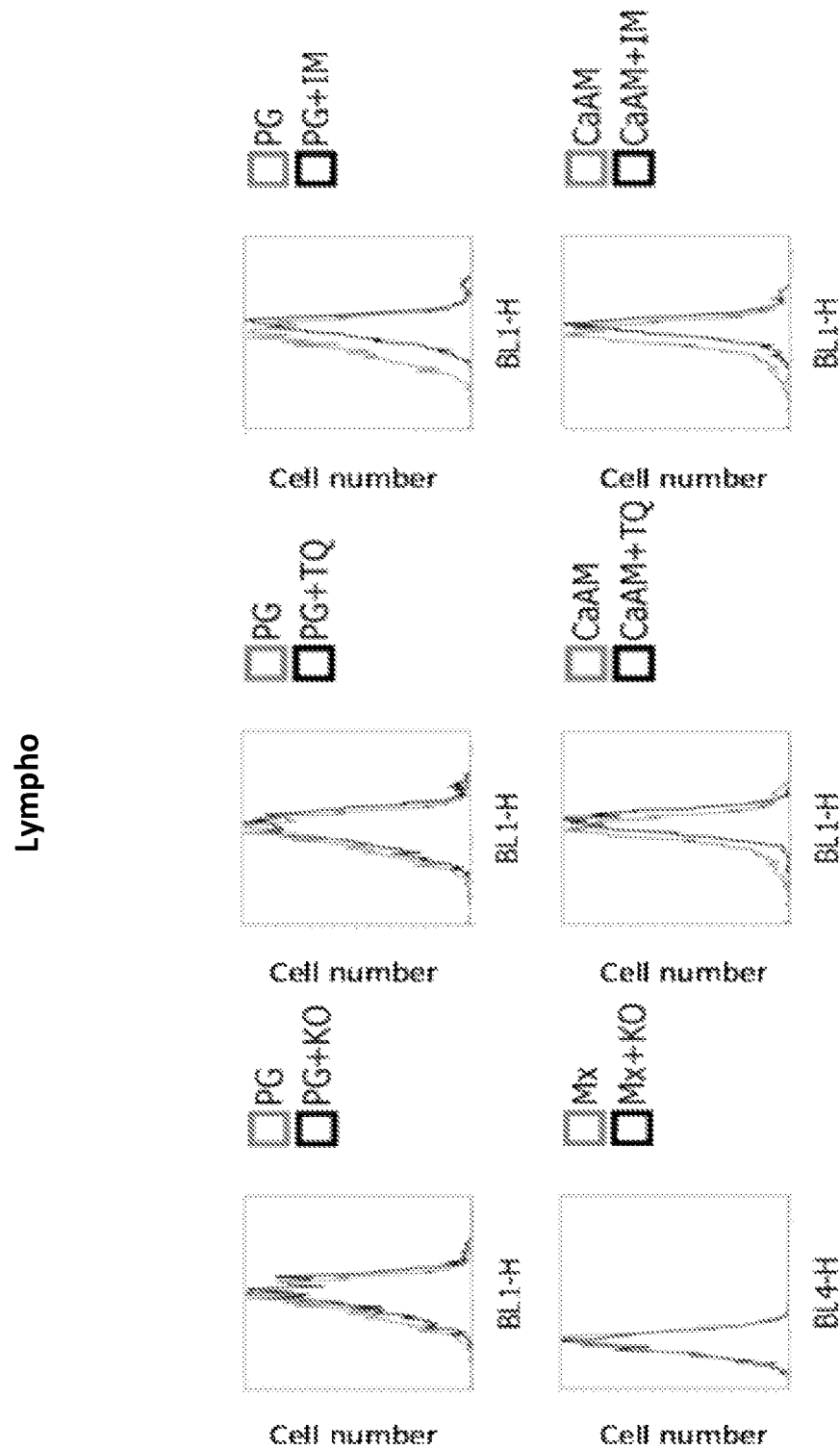
Figure 15C:
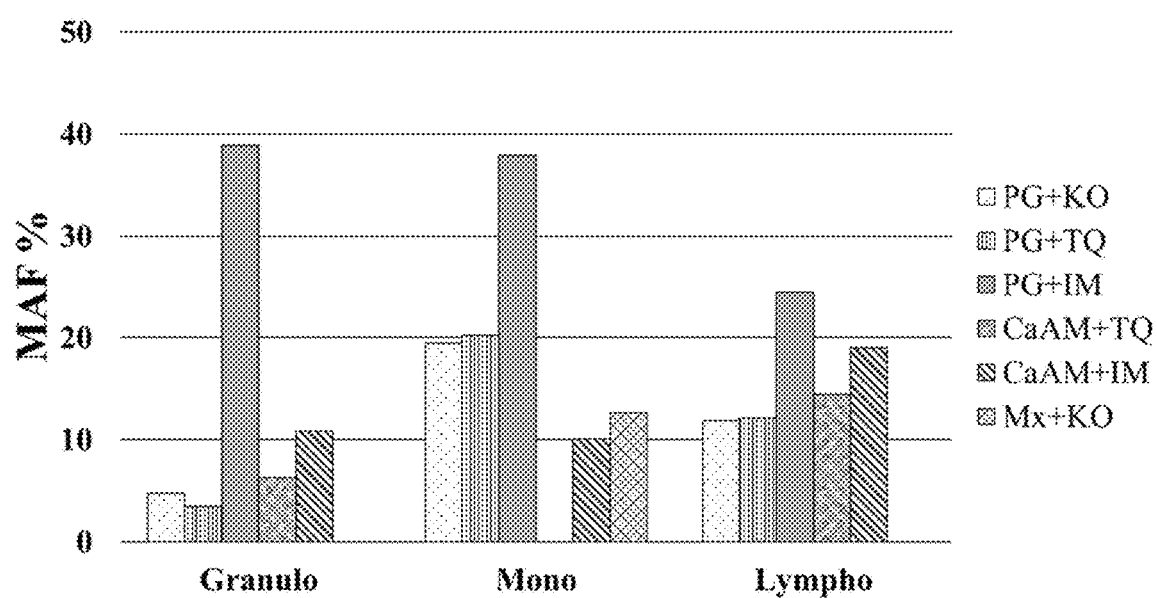

In order to compare the efficiency of PG accumulation to determine the MDR activity factor, as compared to that when using mitoxantrone (MX) we have performed parallel experiments by using these two systems in ABCB1 (PLB cells) and ABCC1 (HL-60 cells) expressing cell lines, respectively. As documented in FIG. 14, the PGD assay as similarly or better applicable than MX for calculating the MDR activity factors for both of these transporter proteins.

In experiments directly following the cellular fluorescence by confocal microscopy (FIG. 6), we have also documented the applicability of the PG accumulation assay to follow the activity of the ABCB1 and the ABCC1 multidrug transporters, respectively. PG fluorescence (full grey circles in the cells, typically light sometimes darker grey, originally green) was examined after 30 minutes of the addition of 0.5 μM PGD to the medium, either in the absence or presence of the transporter inhibitors (0.25 μM tariquidar for ABCB1 or 50 μM benzbromarone for ABCC1). The cells were pre-labeled with fluorescent anti-WGA (medium grey circles in the cells, originally red) to indicate the plasma membranes.

Example 4—Effect of PG Accumulation on Cell Viability

In the following experiments we have studied if PG accumulation has an effect on cell viability and cell growth. As serum non-specific esterases rapidly cleave PGD to PG, and metal ions significantly change PG fluorescence PG loading medium had to be applied.

In the first set of these experiments (FIG. 7, Panel A) we used control and ABCG2 expressing PLB cells, incubated in the PGD loading media with or without 0.5 μM PGD for 30 minutes at 37° C. The PGD-treated cells were then sorted based on PG fluorescence by flow cytometry, and the cells were resuspended in RPMI media. Cell growth was estimated by cell counting for 9 days, and dead cells were excluded by TO-PRO-3 staining. On FIG. 7. (Panel A.) the effect of PhenGreen accumulation on cell growth in PLB cells and PLB-ABCG2 cells is shown.

In the second set of experiments HEK or A431 cells were treated with the indicated concentrations of PGD for 30 min at 37° C. in the loading media, then washed and cultured in normal cell culturing media for 72 hours. Live cell number was determined by flow cytometry, dead cells excluded by TO-PRO-3 staining (see Methods). Based on these experiments, the PG accumulation used above for transporter activity studies and cell sorting had no measurable effect on the growth of the cells. On FIG. 7. (Panels B and C.) Cytotoxic effects of PGD treatment in HEK and A431 cells are shown.

Example 5—Measurement of ABCG2, ABCB1 or ABCC1 Transporter Function in Human Samples (PBMC)

A functional test was carried out in human peripheral blood mononuclear cells (PBMCs) by PhenGreen SK diacetate (PGD), Calcein-AM (CaAM) or mitoxantrone (Mx), with or without transporter inhibitors.

Freshly drawn venous blood samples were collected from healthy donors into EDTA coated tubes. Peripheral blood mononuclear cells (PBMCs) were isolated by Ficoll-histopaque density gradient centrifugation. The PBMCs were washed twice with 1 mL EDTA-DPBS uptake buffer (1 mM EDTA and 1 g/L D-glucose with phosphate buffered saline). The various cell populations can be stained with cluster of differentiation markers (CD markers), conjugated by e.g. APC, APC-Cy7, Pacific blue, or other fluorescent marker. After CD labeling the cells were incubated in the uptake buffer with 1 μM PhenGreen SK diacetate (PGD), or 0.25 μM Calcein-AM (CaAM) or 1 μM mitoxantrone (Mx), with or without selective transporter inhibitors, for 30 minutes (PGD and CaAM) or 60 minutes (Mx) at 37° C. For assessing transporter inhibition, the ABCG2 transporter function was inhibited by 2.5 μM KO143 (KO), ABCB1 function by 0.5 μM tariquidar (TQ), and ABCC1 function by 50 μM indomethacine (IM). The reaction was stopped by the addition of ice-cold EDTA-DPBS and fluorescence was measured as described above.

Mononuclear cell populations, i.e. granulocytes, monocytes and lymphocytes have been visualized by flow cytometry as described in the Materials and Methods chapter (Panel A). Flow cytometry measurements based on Phengreen (PG), Calcein (CaAM) and Mitoxantrone (Mx) uptake for the three ABC transporters have been carried out as described in the Materials and Methods (Panel B). MDR activity factors were calculated as described above based on the measurements of the accumulation of the three fluorescent dyes, with or without inhibitors, in the respective leukocyte populations (Panel C). It has been found that the exemplary compound of the invention (PhenGreen SK diacetate) is an active substrate in each cell type, i.e. in each mononuclear cell populations and is suitable for measurement of transport activity. It has also been found that the MAF factor obtained was typically measured to be higher in case of ABCC1 in case of each cell types. In case of monocytes the exemplary compound of the invention provided a higher MAF factor than Calcein AM and mitoxantrone for each of the transporters.

This example also provides evidence that measurement according to the invention can be carried out starting from blood samples and in blood cell populations with a reliable and relevant results.

Example 6—Exemplary Diagnostic Application of the PG Accumulation for the Quantitative Assessment of ABC Transporter Activity in Human Blood Cell Samples A patient with chronic lymphocytic leukemia (CLL), who is refractory to fludarabine, cyclophosphamide, and rituximab (FCR) treatment regimen, is diagnosed. Blood sample is drawn by usual methods. Peripheral blood mononuclear cells are prepared. Measurement of ABC transporter activity is carried out as described in Example 5. ABC activity values are separately obtained for Lymphocytes in case of each of the three ABC transporters by flow cytometry. The level of MDR activity may help with further therapeutic considerations.

CONCLUSIONS

In the above illustrative Examples the present inventors have shown that in various human cells the expression of the multidrug transporters ABCG2, ABCB1 or ABCC1 strongly reduce fluorescent PG accumulation when the cells are incubated with PhenGreen SK diacetate (PGD). The compounds have a low toxicity and highly sensitive in cells and are suitable for use in biological samples e.g. in blood. Other multidrug transporters and fluorescent dyes are considered as and are plausible to be appropriate in the present invention.

INDUSTRIAL APPLICABILITY

It is documented herein that the assay according to the invention can be used for the ABCG2, ABCB1 as well as for the ABCC1 drug transporters, providing a new, unique possibility to examine the functional properties of these key human multidrug transporters by using the same reagents and conditions. In addition, we document that low numbers of ABC transporter positive cells can be distinguished and sorted out from mixed cell populations. The assay is also advantageously applicable for diagnostic purposes for a quantitative determination of the ABC transporter activity in the cells of a diagnostic specimen. Moreover, after a short-term PG accumulation the cells do not show a sign of growth change or toxicity. While DNA-reactive fluorescent transporter substrates may cause major genetic alterations, the cytoplasmic PG accumulation does not seem to have such an effect. Therefore, cell sorting and further selective cell culturing can also be supported by this method.

As a summary, the PGD uptake and PG accumulation assay, complemented with the use of selective transporter inhibitors, is a new, highly sensitive tool to examine the functional properties of the key multidrug transporters, to quantitatively assess the function of drug transporters in cell specimens, and to efficiently select and sort transporter-expressing cells.

REFERENCES

Non-Patent Literature

Alexander S P H, Kelly E, Marrion N, Peters J A, Benson H E, Faccenda E, Pawson A J, Sharman J L, Southan C, Davies J A and CGTP Collaborators (2015) The Concise Guide to PHARMACOLOGY 2015/16: Transporters. Br J Pharmacol. 172: 6110-6202.

Bennett, B. C. 2007. Chapter 3. Twenty-five Important Plant Families. B. C. Bennett, editor. UNESCO Encyclopedia of Life Support Systems. eolss.net.

Boesch M, Reimer D, Rumpold H, Zeimet A G, Sopper S, Wolf D. DyeCycle Violet Used for Side Population Detection is a Substrate of P-Glycoprotein. Cytom Part A. 2012; 517-522. doi:10.1002/cyto.a.22038

Boesch M, Wolf D, Sopper S. Optimized Stem Cell Detection Using the DyeCycle-Triggered Side Population Phenotype. Stem Cells Int. 2016; 2016. doi:10.1155/2016/1652389

Dagur P K and McCoy J P Collection, Storage, and Preparation of Human Blood Cells. Curr Protoc Cytom. 2015; 73: 5.1.1-5.1.16. PMID: 26132177

Dean M, Fojo T, Bates S. Tumour stem cells and drug resistance. Nat Rev. 2005; 5. doi:10.1038/nrc1590

Doyle L A, Ross D D. Multidrug resistance mediated by the breast cancer resistance protein BCRP (ABCG2). Oncogene. 2003; 22: 7340-7358. doi:10.1038/sj.onc.1206938

Elkind N B, Szentpétery Z, Apáti Á, Özvegy-Laczka C, Ujhelly O, Szabo K, et al. Multidrug Transporter ABCG2 Prevents Tumor Cell Death Induced by the Epidermal Growth Factor Receptor Inhibitor Iressa. 2005; 1770-1778.

Hawley T., Hawley R. (eds) Flow Cytometry Protocols. Methods in Molecular Biology (Methods and Protocols), vol 699. Humana Press Hegedűs C, Szakács G, Homolya L, Orbán T I, Telbisz Á, Jani M, et al. Ins and outs of the ABCG2 multidrug transporter: An update on in vitro functional assays. Adv Drug Deliv Rev. 2009; 61: 47-56. doi:10.1016/j.addr.2008.09.007

Holló Z, Homolya L, Hegedűs T, Müller M, Szakács G, Jakab K, et al. Parallel functional and immunological detection of human multidrug resistance proteins, P-glycoprotein and MRP1. Anticancer Res. 1998; 18: 2981-7.

Hollo, Zs, Homolya, Laszlo, Sarkadi, Balazs EP 0784699 B1, filed in 1995, published in 1999

Homolya L, Holló M, Müller M, Mechetner E B, Sarkadi B. A new method for a quantitative assessment of P-glycoprotein-related multidrug resistance in tumour cells. Br J Cancer. 1996; 73: 849-55.

Homolya L, Holló Z, Germanns, Ursula A, Pastan I, Gottesman M M, Sarkadi B. Fluorescent Cellular Indicators are extruded by the Multidrug resistance Protein. J Biol Chem. 1993; 29: 21493-21496.

Homolya L, Orbán T I, Csanády L, Sarkadi B. Mitoxantrone is expelled by the ABCG2 multidrug transporter directly from the plasma membrane. BBA—Biomembr. Elsevier B. V.; 2011; 1808: 154-163. doi:10.1016/j.bamem.2010.07.031

Horsey A J, Cox M H, Sarwat S, Kerr I D. The multidrug transporter ABCG2: still more questions than answers. Biochem Soc Trans. 2016; 44: 824-30. doi:10.1042/BST20160014

Illing A C, Shawki A, Cunningham C L, Mackenzie B. Substrate profile and metal-ion selectivity of human divalent metal-ion transporter-1. J Biol Chem. 2012; 287: 30485-30496. doi:10.1074/jbc.M112.364208;

Kappelmayer, J, Hevessy Zs, Apjok A, Tauberné Jakab, K. et al. Prediction of Therapy Response and Prognosis in Leukemias by Flow Cytometric MDR Assays. EJIFCC. 2013 23(4): 117-123.

Karászi É, Jakab K, Homolya L, Szakács G, Holló Z, Nahajevszky S, et al. Calcein assay for multidrug resistance reliably predicts therapy response and survival rate in acute myeloid leukaemia. Br J Haematol. 2001; 112: 308-314.

László L, Sarkadi B, Hegedűs T. Jump into a New Fold—A Homology Based Model for the ABCG2/BCRP Multidrug Transporter. PLoS One. 2016; 11: 1-22. doi:10.1371/journal.pone.0164426

Lebedeva I V., Pande P, Patton W F. Sensitive and specific fluorescent probes for functional analysis of the three major types of Mammalian ABC transporters. PLoS One. 2011; 6. doi:10.1371/journal.pone.0022429

Márki-Zay J. Tauberné Jakab K. Szerémy P., Krajcsi P. MDR-ABC transporters: biomarkers in rheumatoid arthritis Clin Exp Rheumatol 2013; 31: 779-787

Ma Y, Abbate V, Hider R C. Iron-sensitive fluorescent probes: monitoring intracellular iron pools. Metallomics. Royal Society of Chemistry; 2015; 7: 212-222. doi:10.1039/C4MT00214H Morisaki K, Robey R W, Özvegy-Laczka C, Honjo Y, Polgar O, Steadman K, et al. Single nucleotide polymorphisms modify the transporter activity of ABCG2. Cancer Chemother Pharmacol. 2005; 56: 161-172. doi:10.1007/s00280-004-0931-x Nerada Z, Hegyi Z, Szepesi Á, Tóth S, Hegedűs C, Várady G, et al. Application of fluorescent dye substrates for functional characterization of ABC multidrug transporters at a single cell level. Cytom Part A. 2016; doi:10.1002/cyto.a.22931

Özvegy-Laczka C, Várady G, Köblös G, Ujhelly O, Cervenak J, Schuetz J D, et al. Function-dependent Conformational Changes of the ABCG2 Multidrug Transporter Modify Its Interaction with a Monoclonal Antibody on the Cell Surface. J Biol Chem. 2005; 280: 4219-4227. doi:10.1074/jbc.M411338200

Robey R W, Ierano C, Zhan Z, Bates S E. The Challenge of Exploiting ABCG2 in the Clinic. Curr Pharm Biotechnol. 2012; 12: 595-608.

Salvia, Antonella Maria et al. Expression of some ATP-binding cassette transporters in acute myeloid leukemia. Hematol Rep 2017 9(4) 7406.

Sarkadi B, Homolya L, Szakács G, Váradi A. Human Multidrug Resistance ABCB and ABCG Transporters: Participation in a Chemoimmunity Defense System. Physiol Rev. 2006; 86: 1179-1236. doi:10.1152/physrev.00037.2005.

Sheng Z, Schuetz J D, Bunting K D, Colapietro A-M, JANARDHAN S, Morris J J, et al. The ABC transporter Bcrp1/ABCG2 is expressed in a wide variety of stem cells and is a molecular determinant of the side-population phenotype. Nat Med. 2001; 7: 1028-34. doi:10.1038/nm0901-1028

Strouse J J, Ivnitski-Steele I, Waller A, Young S M, Perez D, Evangelisti A M, et al. Fluorescent substrates for flow cytometric evaluation of efflux inhibition in ABCB1, ABCC1, and ABCG2 transporters. Anal Biochem. 2013; 437: 77-87. doi:10.1016/j.ab.2013.02.018

Szakács G, Váradi A, Özvegy-Laczka C, Sarkadi B. The role of ABC transporters in drug absorption, distribution, metabolism, excretion and toxicity (ADME-Tox). Drug Discov Today. 2008; 13: 379-393. doi:10.1016/j.drudis.2007.12.010

Taylor N M I, Manolaridis I, Jackson S M, Kowal J, Stahlberg H, Kaspar P. Structure of the human multidrug transporter ABCG2. Nature. Nature Publishing Group; 2017; 546: 504-509. doi:10.1038/nature22345

Telford W G, Bradford J, Godfrey W, Robey R W, Bates S E. Side Population Analysis Using a Violet-Excited Cell-Permeable DNA Binding Dye. Stem Cells. 2007; 25: 1029-1036. doi:10.1634/stemcells.2006-0567

PATENTS AND PATENT APPLICATIONS

Kuhn et al, U.S. Pat. No. 5,648,270 granted to Molecular Probes Inc, Jul. 15, 1997

Sarkadi et al., EP0784699B1 Published in 1996;

Sarkadi et al. U.S. Pat. No. 5,872,014 granted on Feb. 19, 1999.

Lebedeva et al. U.S. Pat. No. 9,097,673 granted on Aug. 4, 2015.

The invention claimed is:

1. A method of assessing adenosine triphosphate-binding cassette (ABC) transporter activity of an ABC multidrug transporter that transports hydrophobic or amphipathic heterocycles, comprising:

(a) exposing a population of biological specimen cells and a population of negative control cells to a fluorescein derivative ester compound of Formula Ia to load the biological specimen cells and the negative control cells with the ester compound in a loading medium, wherein the ester compound is hydrolyzed to a corresponding fluorescein derivative hydroxy compound by cellular esterases inside both cells, wherein at least the hydroxy compound is fluorescent;

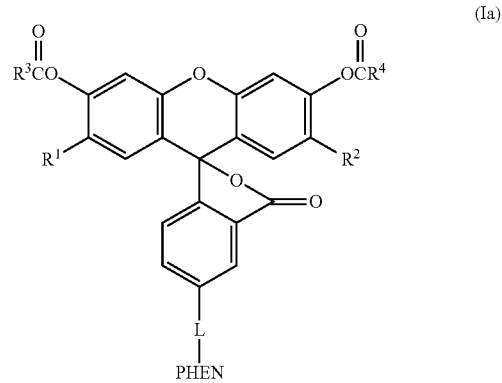

(Ia)

and wherein

R1 and R2 are independently hydrogen, halogen or pseudohalogen,

R3 and R4 are independently methyl, ethyl or propyl,

L is a linker having 2 to 5 chain atoms selected from the group consisting of C and N, the linker forming a conjugated pi electron system with both pi electrons of the fluorescein moiety and of the PH EN moiety, or the L is selected from the group consisting of aminocarbonyl (carboxamide), urea, thiourea, alkenyl, C2 alkenylamine, C4 alkenylamine and C3 alkenylamide, PHEN is a phenantrene derivative comprising 1, 2 or 3 ring nitrogens in any of positions 1 to 8 of the phenantrene skeleton wherein L is covalently bound to PHEN in a position corresponding to positions 9 or 10 of the phenantrene skeleton, and (b) assessing the level of the fluorescein derivative ester compound or the corresponding hydroxy compound or both, accumulating in the specimen cells to obtain a level of the fluorescein derivative compound in the specimen cells and in the population of negative control cells to obtain a negative control level of the fluorescein derivative compound, by assessing the level of fluorescence in the cells, (c) comparing the level of the fluorescein derivative compound in the specimen cells with a negative control level obtained from the negative control cells, and (d) wherein a lower level of the fluorescein derivative compound in the specimen cells compared to the negative control level assesses the level of ABC transporter activity in the biological specimen.

2. The method of claim 1, wherein the ABC multidrug transporter is a multidrug transporter of the B, C or G families of ABC transporters extruding a PhenGreen compound from the cells.

3. The method of claim 2, wherein the multidrug transporter of the B, C or G families is selected from the group consisting of ABCB1 (MDR1, Pgp), ABCC1 (MRP1) and ABCG2 (BCRP).

4. The method of claim 1, wherein the fluorescein derivative ester compound is a compound having general formula (IIb)

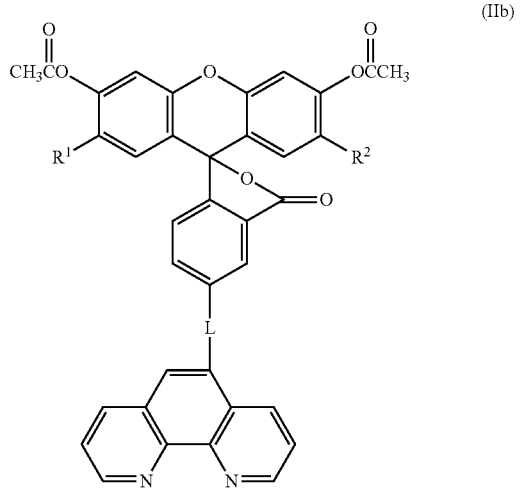

(IIb)

wherein the linker L is selected from the group consisting of aminocarbonyl, urea, thiourea, alkenyl, C2 alkenylamine, C4 alkenylamine and C3 alkenylamide.

5. The method of claim 4, wherein the fluorescein derivative ester compound is PhenGreen FL diacetate or PhenGreen SK diacetate, and the fluorescein derivative hydroxy compound is PhenGreen FL or PhenGreen SK.

6. The method of claim 1, wherein the biological specimen cells are obtained from
a mammalian subject, or
a culture of cells.

7. The method of claim 1, further comprising exposing a test population of cells of the biological specimen cells to a cytotoxic compound, a therapeutic compound and/or a transporter substrate compound.

8. The method of claim 1, wherein the biological specimen cells are biological sample cells obtained from a mammalian subject, and wherein the level of fluorescein derivative compound accumulating in the sample cells is assessed and thereby the ABC transporter activity is assessed in the sample cells.

9. The method of claim 8, wherein the biological sample is a blood sample, a blood derived sample, a sample comprising immune cells, a biopsy sample, or a sample from a tumor tissue.

10. The method of claim 1, wherein the cells of the negative control cell population are selected from the following types of cells:
cells which do not express the ABC transporter protein,
cells which express the ABC transporter protein under a pre-determined threshold value,
cells in which the expression of the ABC transporter protein is silenced,
cells in which express a mutant ABC transporter protein which does not transport the fluorescein derivative ester compound or hydroxy compound, and/or
cells in which the activity of the ABC transporter protein is inhibited.

11. The method of claim 1, wherein comparing the level of the fluorescein derivative compound in the specimen cells with a negative control level comprises a quantitative measurement of ABC transporter activity.

12. The method of claim 11, wherein the quantitative measurement of ABC transporter activity comprises
expressing the level of the fluorescein derivative compound in specimen cells as quantitative value (F) and the negative control level of the fluorescein derivative compound as quantitative value (F*) and
subtracting one of the quantitative values from the other.

13. The method of claim 12, wherein comparing the level of the fluorescein derivative compound in specimen cells with a negative control level comprises expressing the level of the fluorescein derivative compound in specimen cells as quantitative value (F) of the fluorescein derivative compound within the specimen cells; and then expressing the negative control level of the fluorescein derivative compound as a quantitative value (F*) of the fluorescein derivative compound in the negative control cell, and calculating multidrug resistance activity factor (MAF) that is illustrative of the measure of the activity of the ABC transport protein present in the specimen cells using the correlation: MAF= (F*−F)/F*.

14. The method of claim 7, wherein
the level of the fluorescein derivative compound in specimen cells of the test population is quantitatively determined as a test multidrug resistance activity factor (MAF) value and
the level of the fluorescein derivative compound in the reference population is also quantitatively determined as a reference MAF value, and
the effect of the test compound to the ABC transporter activity is assessed by comparison of MAF values.

15. The method of claim 1, further comprising using a fluorometry, a flow cytometry and/or a fluorescence microscopy.

16. The method of claim 1, further comprising one or more of the following steps:
   measuring the survival of cells in the biological specimen,
   determining the amount of a multi-drug transporter protein made by the biological specimen cells, and
   determining the amount of a multi-drug transporter protein on the surface of the biological specimen cells.

17. The method of claim 5, wherein the biological specimen is selected from
   a biological sample obtained from a subject, or
   a culture of cells.

18. The method of claim 7, further comprising using a fluorometry, a flow cytometry and/or a fluorescence microscopy.

19. The method of claim 1, wherein the method is a selection method, and wherein cells having the ABC transporter activity measured in the biological specimen are selected.

20. The method of claim 1, wherein R1 and R2 are independently selected from H and Cl or from Cl and F.

21. The method of claim 1, wherein R1 and R2 are identical.

22. The method of claim 1, wherein R3 and R4 are independently methyl or ethyl.

23. The method of claim 1, wherein PHEN is a phenantrene derivative comprising 2 ring nitrogens.

* * * * *